(12) United States Patent
Demuth et al.

(10) Patent No.: US 12,215,104 B2
(45) Date of Patent: Feb. 4, 2025

(54) ANTI-BIOFILM COMPOUNDS

(71) Applicant: UNIVERSITY OF LOUISVILLE RESEARCH FOUNDATION, INC., Louisville, KY (US)

(72) Inventors: Donald R. Demuth, Louisville, KY (US); Frederick A. Luzzio, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1028 days.

(21) Appl. No.: 17/263,126

(22) PCT Filed: Jul. 19, 2019

(86) PCT No.: PCT/US2019/042676
§ 371 (c)(1),
(2) Date: Jan. 25, 2021

(87) PCT Pub. No.: WO2020/023318
PCT Pub. Date: Jan. 30, 2020

(65) Prior Publication Data
US 2021/0188838 A1    Jun. 24, 2021

Related U.S. Application Data

(60) Provisional application No. 62/711,248, filed on Jul. 27, 2018.

(51) Int. Cl.
| | |
|---|---|
| C07D 419/14 | (2006.01) |
| A61K 45/06 | (2006.01) |
| A61P 31/04 | (2006.01) |
| C07D 419/12 | (2006.01) |

(52) U.S. Cl.
CPC ............ *C07D 419/14* (2013.01); *A61K 45/06* (2013.01); *A61P 31/04* (2018.01); *C07D 419/12* (2013.01)

(58) Field of Classification Search
CPC ..... C07D 419/14; C07D 419/12; A61P 31/04; A61K 45/06
USPC ........................................................ 514/245
See application file for complete search history.

(56) References Cited

U.S. PATENT DOCUMENTS 9,167,820 B2 * 10/2015 Demuth et al. ...... C07D 413/06
2014/0161845 A1   6/2014 Demuth et al.

OTHER PUBLICATIONS

Aliko, A., et al., "Discovery of Novel Potential Reversible Peptidyl Arginine Deiminase Inhibitor", Int J Mol Sci 20, 2174, 1-16 (2019).
Dominy, S., et al., "Porphyromonas gingivalis in Alzheimer's disease brains: Evidence for disease causation and treatment with small-molecule inhibitors", Sci Adv 5, eaau3333, 1-21 (2019).
Ho, M., et al., "Two Small Molecules Block Oral Epithelial Cell Invasion by Porphyromons gingivalis", PLoS One 11(2), e0149618, 1-12 (2016).

(Continued)

*Primary Examiner* — Jeffrey S Lundgren
*Assistant Examiner* — Heather Dahlin
(74) *Attorney, Agent, or Firm* — Viksnins Harris Padys Malen LLP

(57) ABSTRACT

The present invention provides non-peptide compounds that mimic the streptococcal SspB Adherence Region (BAR) and function as inhibitors of *P. gingivalis* adherence to streptococci. The invention also provides methods of making and using the inhibitors.

12 Claims, 4 Drawing Sheets

(56) References Cited

OTHER PUBLICATIONS

Kalimuthu, S , et al., "A Novel Small Molecule, 1,3-di-m-tolyl-urea, Inhibits and Disrupts Multispecies Oral Biofilms", Microorganisms 8, 1261, 1-12 (2020).

Luzzio, P , et al., "Synthesis of Extended Oxazoles III: Reactions of 2-(Phenylsulfonyl)methyl-4,5-diaryloxazoles", J Org Chem 81, 10521-10526 (2016).

Patent Cooperation Treaty , International Searching Authority, Search Report and Written Opinion for PCT/US2019/042676, 8 pages, dated Oct. 10, 2019.

Patil, P , et al., "1,2,3-Triazole-based inhibitors of Porphyromonas gingivalis adherence to oral streptococci and biofilm formation", Bioorganic & Medicinal Chemistry 24, 5410-5417 (2016).

Stone, V , et al., "Identification of Small-Molecule Inhibitors against Meso-2, 6-Diaminopimelate Dehydrogenase from Porphyromonas gingivalis", PLoS One 10(11), e0141126, 1-24 (2015).

Tan, J , et al., "In Vitro and In Vivo Activity of Peptidomimetic Compounds That Target the Periodontal Pathogen Porphyromonas gingivalis", Antimicrobial Agents and Chemotherapy 62(7), e00400-18, 12 pages (2018).

Wright, C , et al., "Disruption of heterotypic community development by Porphyromonas gingivalis with small molecule inhibitors", Mol Oral Microbiol 29(5), 185-193 (2014).

\* cited by examiner

Figure 2A                    Figure 2B
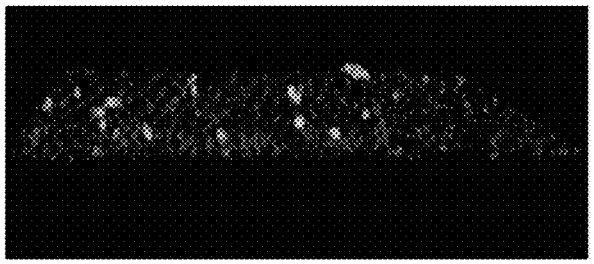
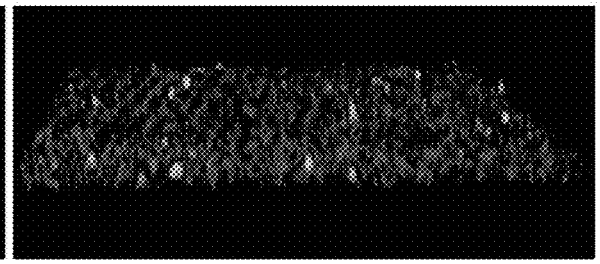
Figure 2C                    Figure 2D

ANTI-BIOFILM COMPOUNDS

CROSS-REFERENCE TO RELATED APPLICATION

This application claims priority to U.S. Provisional Application No. 62/711,248, filed on Jul. 27, 2018. The entire content of the application referenced above is hereby incorporated by reference herein.

BACKGROUND

Adult periodontitis is associated with elevated levels of several Gram negative organisms in the subgingival oral biofilm, including the asaccharolytic, obligate anaerobe *Porphyromonas gingivalis*. In this primary niche, *P. gingivalis* interacts with a variety of other Gram negative obligate and facultative anaerobes, such as *Fusobacterium nucleatum, Treponema denticola*, and *Tannerella forsythus* through specific receptor-ligand interactions. However, the initial colonization of the oral cavity by *P. gingivalis* likely occurs through adherence to organisms in the supragingival biofilm and the successful colonization of this niche by *P. gingivalis* is contingent upon a variety of factors such as reduced oxygen tension and sufficient nutritional sources. Consistent with this, *P. gingivalis* has been shown to also adhere to organisms in supragingival plaque that may provide it with physiologic support, such as *Streptococcus gordonii* and *F. nucleatum*.

SUMMARY

The present invention provides therapies to treat or prevent the onset of periodontal disease, one of the most common bacterial infections of humans (~35% of the adult population worldwide exhibits symptoms of periodontal disease). Because the target for the inhibiting compound is the adherence of *P. gingivalis* to supragingival plaque, it is effective in mouth rinses and toothpaste formulations. Such formulations are easily and non-invasively administered by dental practitioners during routine office visits, or are developed into consumer products for home use. *P. gingivalis* gains systemic exposure through damage to gingival tissues. Therefore, limiting the *P. gingivalis* adherence to supragingival plaque in the oral cavity has a dramatic effect on systemic diseases that are associated with the organism, such as atherosclerosis and heart disease.

Current treatment for periodontitis involves removal of all bacteria from the subgingival pockets. Removal of subgingival plaque by current treatment methods is temporary, since the subgingival packet may be re-colonized after cleaning by organisms from the supragingival reservoir. The present technology is specific for the pathogenic organism and will likely not influence the benign or helpful organisms that inhabit the oral cavity. There are currently no pathogen specific treatments available for oral diseases such as periodontal disease. The present inhibiting compound provides long term control of *P. gingivalis* populations in the oral cavity because it prevents the initial formation of *P. gingivalis* biofilms, as well as disrupting pre-existing biofilms. It is formulated in a way to allow daily exposure allowing it to target organisms in the reservoir in supragingival plaque.

The present invention provides a compound of formula I:

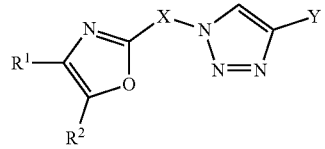

wherein:

X is —($CH_2$)S(=O)$_n$phenyl-; or

X is phenyl and (a) at least one of $R^1$ or $R^2$ is an optionally substituted 5-6 membered heteroaryl; or (b) Y is heteroaryl, ($C_3$-$C_7$)carbocycle, or aryl wherein the heteroaryl, ($C_3$-$C_7$)carbocycle, or aryl is substituted with at least one —$NR_jR_k$ wherein at least one of Rj or Rk is optionally substituted phenyl and wherein the heteroaryl, ($C_3$-$C_7$)carbocycle, or aryl is further optionally substituted with one or more $Z^1$ groups;

n is 1 or 2;

Y is heteroaryl, ($C_3$-$C_7$)carbocycle, or aryl wherein any heteroaryl, ($C_3$-$C_7$)carbocycle, or aryl of Y is optionally substituted with one or more $Z^1$ groups;

$R^1$ is ($C_1$-$C_8$)alkyl, ($C_2$-$C_8$)alkenyl, ($C_2$-$C_8$)alkynyl, aryl, or 5-6 membered heteroaryl wherein the aryl or 5-6 membered heteroaryl is optionally substituted with one or more groups selected from the group consisting of ($C_1$-$C_8$)alkyl, ($C_2$-$C_8$)alkenyl, ($C_2$-$C_8$)alkynyl, ($C_3$-$C_7$)carbocycle, halo($C_1$-$C_3$)alkyl, —CN, $NO_2$, halogen, —$OR_a$, —$SR_a$, —S(O)$_2$$NR_bR_c$, —$NR_bR_c$, —$NR_aCOR_d$, —C(O)$R_a$, —C(O)O$R_a$, and —C(O)$NR_bR_c$;

$R^2$ is ($C_1$-$C_8$)alkyl, ($C_2$-$C_8$)alkenyl, ($C_2$-$C_8$)alkynyl, aryl, or 5-6 membered heteroaryl wherein the aryl or 5-6 membered heteroaryl is optionally substituted with one or more groups selected from the group consisting of ($C_1$-$C_8$)alkyl, ($C_2$-$C_8$)alkenyl, ($C_2$-$C_8$)alkynyl, ($C_3$-$C_7$)carbocycle, halo($C_1$-$C_3$)alkyl, —CN, $NO_2$, halogen, —$OR_e$, —$SR_e$, —S(O)$_2$$NR_fR_g$, —$NR_fR_g$, —$NR_eCOR_h$, —C(O)$R_e$, —C(O)O$R_e$, and —C(O)$NR_fR_g$;

each $R_a$ is independently selected from the group consisting of H, ($C_1$-$C_6$)alkyl, ($C_2$-$C_8$)alkenyl, ($C_2$-$C_8$)alkynyl, ($C_3$-$C_7$)carbocycle, and aryl;

$R_b$ and $R_c$ are each independently selected from the group consisting of H, ($C_1$-$C_8$)alkyl, ($C_2$-$C_8$)alkenyl, ($C_2$-$C_8$)alkynyl, ($C_3$-$C_7$)carbocycle and aryl, or $R_b$ and $R_c$ together with the nitrogen to which they are attached form a 5, 6 or 7-membered heterocycle;

$R_d$ is independently selected from the group consisting of ($C_1$-$C_8$)alkyl, ($C_2$-$C_8$)alkenyl, ($C_2$-$C_8$)alkynyl, ($C_3$-$C_7$)carbocycle, and aryl;

each $R_e$ is independently selected from the group consisting of H, ($C_1$-$C_8$)alkyl, ($C_2$-$C_8$)alkenyl, ($C_2$-$C_8$)alkynyl, ($C_3$-$C_7$)carbocycle, and aryl;

$R_f$ and $R_g$ are each independently selected from the group consisting of H, ($C_1$-$C_8$)alkyl, ($C_2$-$C_8$)alkenyl, ($C_2$-$C_8$)alkynyl, ($C_3$-$C_7$)carbocycle and aryl, or $R_f$ and $R_g$ together with the nitrogen to which they are attached form a 5, 6 or 7-membered heterocycle;

$R_h$ is selected from the group consisting of ($C_1$-$C_8$)alkyl, ($C_2$-$C_8$)alkenyl, ($C_2$-$C_8$)alkynyl, ($C_3$-$C_7$)carbocycle and aryl;

each $Z^1$ is independently selected from the group consisting of halogen, ($C_1$-$C_8$)alkyl, ($C_2$-$C_8$)alkenyl, ($C_2$-$C_8$)alkynyl, ($C_1$-$C_6$)haloalkyl, —$OR_i$, —$NR_jR_k$ and —$NR_iCOR_m$;

$R_i$ is H, ($C_1$-$C_6$)alkyl, ($C_1$-$C_6$)haloalkyl or phenyl wherein phenyl is optionally substituted with one or more halogen or ($C_1$-$C_6$)alkyl;

$R_j$ and $R_k$ are each independently selected from H, ($C_1$-$C_8$)alkyl or phenyl wherein phenyl is optionally substituted with one or more halogen or ($C_1$-$C_6$)alkyl;

$R_m$ is ($C_1$-$C_6$)alkyl or a salt thereof.

The terms "protein," "peptide" and "polypeptide" are used interchangeably herein. Peptide sequences specifically recited herein are written with the amino terminus on the left and the carboxy terminus on the right.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

BRIEF DESCRIPTION OF FIGURES

FIGS. 2A-2D. Inhibition of *P. gingivalis/S. gordonii* biofilm formation by compound 102. Biofilms were treated with PBS (FIG. 2A), or 5 µM (FIG. 2B), 20 µM (FIG. 2C), or 40 µM (FIG. 2D) compound 102.

DETAILED DESCRIPTION

Figure 1:
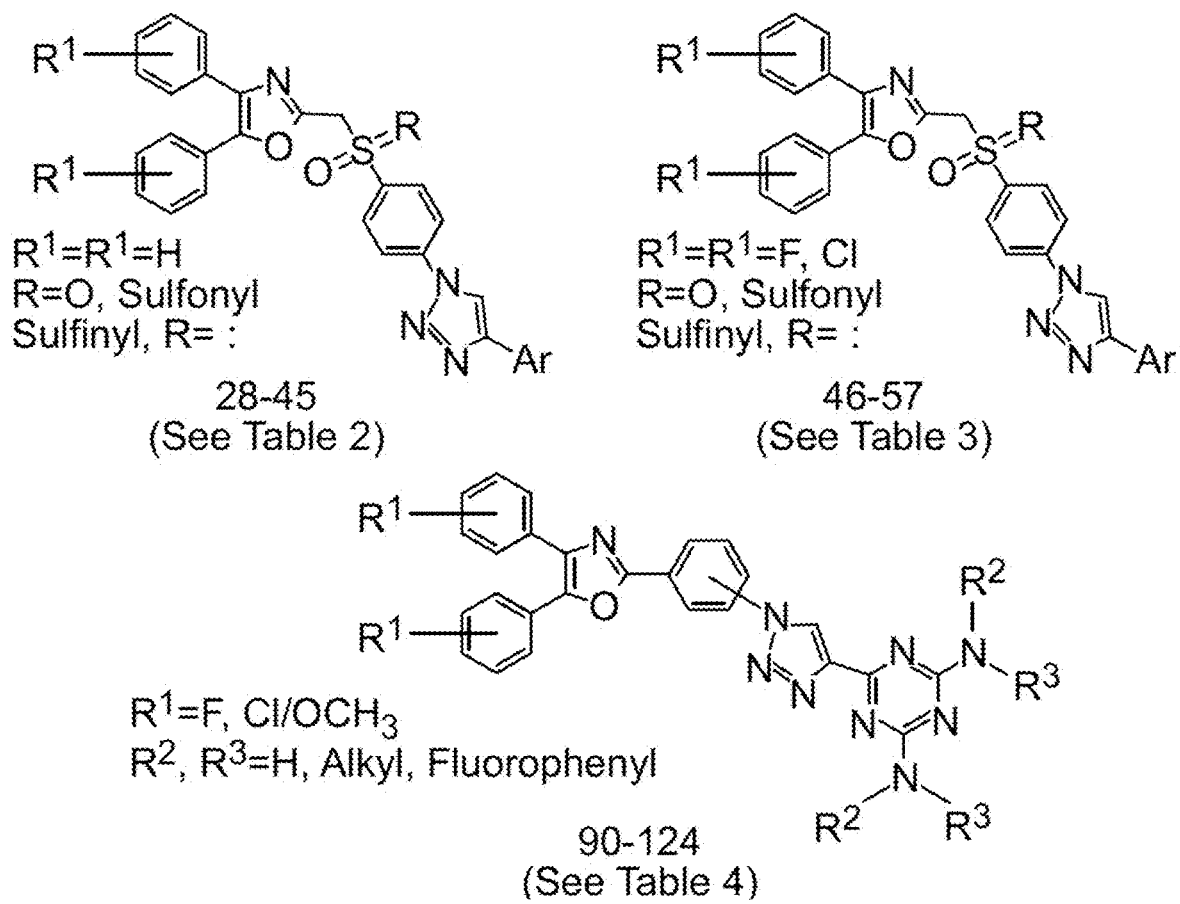
FIG. 1. Second-Generation Inhibitors: Group I (28-45), Group II (46-57), and Group III (90-124).

*P. gingivalis* is strongly associated with adult periodontitis and is also linked to atherosclerosis, heart disease and pre-term births. In the oral cavity, this organism resides in the subgingival pocket and exists in concert with a complex microbial community called a biofilm (dental plaque). However, to reach its primary niche in the subgingival pocket, *P. gingivalis* must first attach to bacterial cells that are present in supragingival dental plaque. *P. gingivalis* colonizes supragingival plaque by adhering to organisms such as *Streptococcus gordonii*. Thus, supragingival plaque may represent a biologic reservoir for *P. gingivalis* in the oral cavity. Because the *P. gingivalis-S. gordonii* interaction represents one of the first reactions that allows *P. gingivalis* to colonize the oral cavity, it is a good target for therapeutic intervention of periodontitis and systemic diseases associated with *P. gingivalis*. Controlling and/or preventing this pathogen from occupying its supragingival niche may limit its access to the preferred subgingival niche that is essential for *P. gingivalis* to exert its pathogenic properties.

Adherence of *P. gingivalis* to *S. gordonii* is mediated by a protein-protein interaction between the fimbrial protein Mfa of *P. gingivalis* and the streptococcal antigen I/II polypeptide. The inventors have dissected this interaction and have identified a specific peptide derived from antigen I/II that binds to Mfa and potently inhibits ($I_{50}$=1.3 µM) the development of *P. gingivalis* biofilms on streptococci. Site specific mutagenesis studies identified a structural motif comprised of the amino acids NITVK (SEQ ID NO:2) that was essential for biofilm inhibitory activity of the peptide. This region alone is not sufficient for biofilm inhibition. An second motif is also required, which includes the amino acids VXXLL (SEQ ID NO:1), where X is any amino acid. Either motif alone is inactive for inhibition of *P. gingivalis* biofilm formation.

A "biofilm" is a complex organization of bacteria that are anchored to a surface via a bacterially extruded exopolysaccharide matrix, and grow into differentiated towers that can be several hundred bacteria in height. The extruded exopolysaccharide matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because or a lack of accessibility by immunoglobulin and complement. The attachment of bacteria to a surface triggers the expression of a cassette of genes, which results in the formation of a biofilm. A "biofilm phenotype" confers to a bacterium with reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces.

Compounds of the Present Invention

Unless stated otherwise, the following terms and phrases as used herein are intended to have the following meanings:

"Alkyl" is a straight or branched hydrocarbon. For example, an alkyl group can have 1 to 20 carbon atoms (i.e, ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl and (t-Bu, —$C(CH_3)_3$.

"Alkenyl" is a straight or branched hydrocarbon containing at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon containing at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1, 2, 3, 4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl", "heterocyclic" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4, 5]decane, etc), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It is to be understood that for compounds of the invention when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diastereomer. In another embodiment, a compound of the invention may be at least 51% a single diastereomer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

Specific embodiments listed below are for compounds of formula I. It is to be understood that two or more embodiments may be combined.

In one embodiment X is —(CH$_2$)S(=O)nphenyl-.

In one embodiment $R^1$ is aryl, or 5-6 membered heteroaryl wherein the aryl or 5-6 membered heteroaryl is optionally substituted with one or more groups independently selected from the group consisting of (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_a$, —SR$_a$, —S(O)$_2$NR$_b$R$_c$, —NR$_b$R$_c$, —NR$_a$COR$_d$, —C(O)R$_a$, —C(O)OR$_a$, and —C(O)NR$_b$R$_c$.

In one embodiment $R^1$ is phenyl or 5-6 membered heteroaryl wherein the phenyl or 5-6 membered heteroaryl is optionally substituted with one or more groups independently selected from the group consisting of (C$_1$-C$_8$)alkyl, halo(C$_1$-C$_3$)alkyl, or halogen, In one embodiment $R^1$ is phenyl wherein the phenyl is optionally substituted with one or more groups independently selected from the group consisting of halogen.

In one embodiment $R^1$ is phenyl, fluorophenyl, or chlorophenyl.

In one embodiment $R^1$ is phenyl, 4-fluorophenyl, or 4-chlorophenyl.

In one embodiment $R^2$ is aryl, or 5-6 membered heteroaryl wherein the aryl or 5-6 membered heteroaryl is optionally substituted with one or more groups independently selected from the group consisting of (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_e$, —SR$_e$, —S(O)$_2$NR$_f$R$_g$, —NR$_f$R$_g$, —NR$_e$COR$_h$, —C(O)R$_e$, —C(O)OR$_e$, and —C(O)NR$_f$R$_g$.

In one embodiment $R^2$ is phenyl or 5-6 membered heteroaryl wherein the phenyl or 5-6 membered heteroaryl is optionally substituted with one or more groups independently selected from the group consisting of (C$_1$-C$_8$)alkyl, halo(C$_1$-C$_3$)alkyl, or halogen.

In one embodiment $R^2$ is phenyl wherein the phenyl is optionally substituted with one or more groups independently selected from the group consisting of halogen.

In one embodiment $R^2$ is phenyl, fluorophenyl, or chlorophenyl.

In one embodiment $R^2$ is phenyl, 4-fluorophenyl, or 4-chlorophenyl.

In one embodiment Y is heteroaryl or aryl wherein any heteroaryl, or aryl of Y is optionally substituted with one or more $Z^1$ groups.

In one embodiment Y is pyridyl, phenyl, or naphthyl wherein any pyridyl, phenyl, or naphthyl of Y is optionally substituted with one or more $Z^1$ groups.

In one embodiment each $Z^1$ is independently selected from the group consisting of halogen, (C$_1$-C$_8$)alkyl, (C$_1$-C$_6$)haloalkyl, or —OR$_i$.

In one embodiment Y is pyridinyl, fluorophenyl, methoxyphenyl, trifluoromethylphenyl, methoxynaphthyl, pentylphenyl, phenoxyphenyl, or di-(trifluoromethy)phenyl.

In one embodiment Y is pyridine-3-yl, 4-fluorophenyl, 3-fluorophenyl, 2-methoxyphenyl, 2 (trifluoromethyl)phenyl, 6-methoxynaphthyl, 4-(n-pentyl)phenyl, 4-(phenoxy)phenyl, or 3,5-di-(trifluoromethy)phenyl.

One embodiment provides a compound selected from compounds 28-57 or a salt thereof.

In one embodiment X is phenyl.

In one embodiment $R^1$ is aryl, or 5-6 membered heteroaryl wherein the aryl or 5-6 membered heteroaryl is optionally substituted with one or more groups independently selected from the group consisting of (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_a$, —SR$_a$, —S(O)$_2$NR$_b$R$_c$, —NR$_b$R$_c$, —NR$_a$COR$_d$, —C(O)R$_a$, —C(O)OR$_a$, and —C(O)NR$_b$R$_c$.

In one embodiment $R^1$ is phenyl or 5-6 membered heteroaryl wherein the phenyl or 5-6 membered heteroaryl is optionally substituted with one or more groups independently selected from the group consisting of (C$_1$-C$_8$)alkyl, halo(C$_1$-C$_3$)alkyl, halogen, or —OR$_a$, In one embodiment $R^1$ is phenyl or furyl wherein the phenyl or furyl is optionally substituted with one or more groups independently selected from the group consisting of halogen or methoxy.

In one embodiment $R^1$ is phenyl, fluorophenyl, chlorophenyl, methoxyphenyl, furyl, In one embodiment $R^1$ is phenyl, 4-fluorophenyl, or 4-chlorophenyl, 4-methoxyphenyl, or 2-furyl.

In one embodiment $R^2$ is aryl, or 5-6 membered heteroaryl wherein the aryl or 5-6 membered heteroaryl is optionally substituted with one or more groups independently selected from the group consisting of (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_e$, —SR$_e$, —S(O)$_2$NR$_f$R$_g$, —NR$_f$R$_g$, —NR$_e$COR$_h$, —C(O)R$_e$, —C(O)OR$_e$, and —C(O)NR$_f$R$_g$.

In one embodiment $R^2$ is phenyl or 5-6 membered heteroaryl wherein the phenyl or 5-6 membered heteroaryl is optionally substituted with one or more groups independently selected from the group consisting of (C$_1$-C$_8$)alkyl, halo(C$_1$-C$_3$)alkyl, halogen, or —OR$_e$.

In one embodiment $R^2$ is phenyl or furyl wherein the phenyl or furyl is optionally substituted with one or more groups independently selected from the group consisting of halogen or methoxy.

In one embodiment $R^2$ is phenyl, fluorophenyl, chlorophenyl, methoxyphenyl, furyl, In one embodiment $R^2$ is phenyl, 4-fluorophenyl, or 4-chlorophenyl, 4-methoxyphenyl, or 2-furyl.

In one embodiment Y is heteroaryl optionally substituted with one or more $Z^1$ groups.

In one embodiment Y is triazinyl optionally substituted with one or more $Z^1$ groups.

In one embodiment each $Z^1$ is independently selected from —NR$_j$R$_k$.

In one embodiment each $R_j$ and $R_k$ is independently selected H, ethyl, or fluorophenyl.

In one embodiment each $R_j$ and $R_k$ is independently selected H, ethyl, 2-fluorophenyl, or 4-fluorophenyl.

One embodiment provides a compound selected from 98-124 or a salt thereof.

One embodiment provides a compound selected from 90-97 or a salt thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

In one embodiment of the invention a salt is a pharmaceutically acceptable salt.

Compositions and Methods of Use

The present invention provides a composition including the compound of formula I and a physiologically acceptable carrier. In certain embodiments, the carrier is a mouth rinse, toothpaste, dental floss or chewing gum. In certain embodiments, the carrier is a polymer.

The present invention provides a therapeutic method for preventing or treating a pathological condition or symptom in a mammal, such as a human, wherein an antibiotic activity is implicated and antagonism of its action is desired, by administering to a mammal in need of such therapy, an effective amount of a compound of formula I.

The present invention provides a therapeutic method for preventing or treating a pathological condition or symptom in a mammal, such as a human, wherein anti-biofilm formation activity is implicated and antagonism of its action is desired, comprising administering to a mammal in need of such therapy, an effective amount of a compound of formula I.

The present invention provides a method to treat a microbial infection comprising administering a therapeutically effective amount of a compound of formula I to a mammal. In certain embodiments, the bacteria are gram-negative bacteria, such as, for example, *Porphyromonas gingivalis*.

The present invention provides a compound of formula I for use in medical therapy.

The present invention provides the use of a compound of formula I for the manufacture of a medicament useful for the treatment of a microbial infection in a mammal.

The present invention provides a method of preventing the adhesion of bacteria on a solid substrate comprising contacting the solid substrate with a compound of formula I. In certain embodiments, the compound is dispersed in a polymer.

The present invention provides a method of preventing the formation of a biofilm of bacteria on a solid substrate comprising contacting the solid substrate with a compound of formula I.

The present invention provides a method of preventing the formation of a biofilm of bacteria in vivo comprising contacting a tissue surface with a compound of formula I. In certain embodiments, the tissue is oral or lung tissue. In certain embodiments, the tissue is a mucosal surface. In certain embodiments, the bacteria are gram-negative bacteria, such as, for example, *Porphyromonas gingivalis*.

The compounds of the present invention can be formulated as consumer product compositions and administered to a mammalian host, such as a human in a variety of forms adapted to the chosen route of administration, e.g., orally. In certain embodiments the compound is included in a toothpaste, a mouth rinse or as a coating on a dental floss.

Further, the compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The present invention provides a therapeutic method for preventing or treating a pathological condition or symptom in a mammal (e.g. a human) in need of such therapy, wherein an antibiotic activity is desired, comprising administering to the mammal an effective amount of a compound a compound of formula I or a pharmaceutically acceptable salt thereof.

The present invention provides a therapeutic method for preventing or treating a pathological condition or symptom in a mammal (e.g. a human) in need of such therapy, wherein anti-biofilm formation is desired, comprising administering to the mammal an effective amount of a compound of formula I or a pharmaceutically acceptable salt thereof.

The present invention provides a method to treat a microbial infection in a mammal (e.g. a human) comprising administering a therapeutically effective amount of a compound of formula I or a pharmaceutically acceptable salt thereof to the mammal.

The present invention provides a compound of formula I as described in any one of claims or a pharmaceutically acceptable salt thereof.

The present invention provides the use of a compound of formula I or a pharmaceutically acceptable salt thereof for the manufacture of a medicament for the treatment of a microbial infection in a mammal.

The present invention provides a method of preventing the adhesion of bacteria on a solid substrate comprising contacting the solid substrate with a compound of formula I or a salt thereof.

The present invention provides a method of preventing the formation of a biofilm of bacteria on a solid substrate comprising contacting the solid substrate with a compound of formula I or a salt thereof.

The present invention provides a method of preventing the formation of a biofilm of bacteria in vivo comprising contacting a tissue surface with a compound of formula I or a pharmaceutically acceptable salt thereof.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful as antibiotics. Examples of such agents include a protein synthesis inhibitor, a cell wall growth inhibitor, a cell membrane synthesis inhibitor, a nucleic acid synthesis inhibitor, or a competitive enzyme inhibitor. In certain embodiments, the additional agent is an antibiotic such as penicillin, ampicillin, amoxicillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraaminosalicylic acid, or ethambutol.

In certain embodiments, the compound of the invention is contacted with a microbe.

Accordingly, in one embodiment the invention also provides a composition comprising a compound of the present invention, at least one other therapeutic agent, and a pharmaceutically acceptable diluent or carrier. The invention also provides a kit comprising a compound of the present invention, at least one other therapeutic agent, packaging material, and instructions for administering the compound of the present invention or the pharmaceutically acceptable salt thereof and the other therapeutic agent or agents to an animal to prevent bacterial infection.

The present invention also provides a solution that includes a solvent, a polymer dissolved in the solvent and a compound of formula I dispersed in the solvent.

Solid Substrates

In one embodiment of the invention, a solution which includes a solvent, a polymer dissolved in the solvent and a compound of formula I dispersed in the solvent is applied to a solid substrate and then the solvent is evaporated. The inclusion of a polymer in intimate contact with a compound of formula I on the underlying solid substrate allows the compound to be retained on the solid substrate in a resilient matrix during expansion of the solid substrate and also slows the administration of drug following implantation. The method can be applied whether the solid substrate has a metallic or polymeric surface. The method is also an extremely simple method since it can be applied by simply immersing the solid substrate into the solution or by spraying the solution onto the solid substrate. The amount of compound to be included on the solid substrate can be readily controlled by applying multiple thin coats of the solution while allowing it to dry between coats. The overall coating should be thin enough so that it will not significantly increase the profile of the solid substrate. It is therefore preferably less than about 0.002 inch thick and most preferably less than 0.001 inch thick. The adhesion of the coating and the rate at which the compound of formula I is delivered can be controlled by the selection of an appropriate bioabsorbable or biostable polymer and by the ratio of the compound if formula I to polymer in the solution. By this method, the compound can be applied to a solid substrate, be retained on a solid substrate during expansion of the solid substrate, and elute the compound at a controlled rate. The release rate can be further controlled by varying the ratio of compound to polymer in the multiple layers. The release rate can be further controlled by varying the ratio of compound to polymer in the multiple layers. For example, a higher compound-to-polymer ratio in the outer layers than in the inner layers would result in a higher early dose which would decrease over time. Examples of some suitable combinations of polymers and solvent are set forth in Table A below.

TABLE A

| Polymer | Solvent |
| --- | --- |
| poly(L-lactic acid) | chloroform |
| poly(lactic acid-co-glycolic acid) | acetone |
| polyether | N-methyl |
| urethane | pyrrolidone |
| silicone adhesive | xylene |
| poly(hydroxy-butyrate-co-hydroxyvalerate) | dichloro-methane |

The present invention further provides a coated device that includes (a) a solid substrate; and (b) a solid composite of a compound of Formula I and a therapeutic substance in an adherent layer on the solid substrate. In certain embodiments, the solid substrate has a metal surface, or a polymeric surface. In certain embodiments, the solid composite includes a plurality of layers. In certain embodiments, the ratio of therapeutic substance to polymer is varied in some of the layers. In certain embodiments, the polymer is a bioabsorbable polymer. In certain embodiments, the polymer is poly(L-lactic acid), poly(lactide-co-glycolide) or poly(hydroxybutyrate-co-valerate). In certain embodiments, the polymer is a biostable polymer. In certain embodiments, the polymer is a silicone, polyurethane, polyester, vinyl homopolymer or copolymer, acrylate homopolymer or copolymer, polyether or cellulosic, or a combination thereof. In certain embodiments, the ratio of compound to polymer in the layer is in the range of about 10:1 to 1:100.

Examples of various polymers used in forming the agent-eluting component include poly(methyl(meth)acrylate ("PMMA"), ethylenevinylalcohol ("EVAL"), poly(butyl (meth)acrylate) ("PBMA"), biodegradable polymers (i.e., Poly(glycolic acid) ("PGA") and poly(L-lactic acid) ("PLLA"), polyethylene glycol ("PEG"), hyaluronic acid ("HA"), polyester amide ("PEA"), poly(glycerol-sebacate) ("PGS"), nanoscale structures of carbon, acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile and other suitable polymers. It is contemplated that the above polymers can be slowly dissolved or chemically degraded or both. As set forth above, the local drug-eluting component alternatively may be fabricated from porous ceramic or various metals or alloys, including stainless steel, platinum, titanium, tantalum, nickel-titanium, cobalt-chromium, and alloys thereof. This family of polymers comprises the following basic components: (1) moieties derived from aliphatic diols, triols, or polyols; (2) moieties derived from polycarboxylic acids (carboxylic acids containing more than one acid functionality); and (3) biobeneficial, non-fouling, or bioactive moieties (U.S. Pat. No. 7,186,789, incorporated by reference herein).

Methods of Manufacture

The present invention provides a method for manufacturing a coated solid substrate by applying to the solid substrate a layer which is a solid composite of polymer and a compound of formula I, wherein the first layer is applied by the steps of: (a) applying to the solid substrate a solution which includes a solvent, a polymer dissolved in the solvent and a compound of formula I dispersed in the solvent; and (b) evaporating the solvent to form a composite of polymer and the inhibitory compound. In certain embodiments, the solution is applied by spraying. In certain embodiments, the solution is applied in a plurality of application and drying steps. In certain embodiments, the ratio of inhibitory compound to dissolved polymer in the solution is varied in some of the plurality of application steps. In certain embodiments, the polymer is a bioabsorbable polymer. In certain embodiments, the polymer is poly(L-lactic acid), poly(lactide-co-glycolide) or poly(hydroxybutyrate-co-valerate). In certain embodiments, the polymer is a biostable polymer. In certain embodiments, the polymer is a silicone, polyurethane, polyester, vinyl homopolymer or copolymer, acrylate homopolymer or copolymer, polyether or cellulosic, or a combination thereof. A typical ratio of compound to dissolved polymer in the solution can vary widely (e.g., in the range of about 10:1 to 1:100).

The invention will now be illustrated by the following non-limiting Examples.

EXAMPLE 1

'Second-Generation' 1,2,3-Triazole-Based Inhibitors of *Porphyromonas Gingivalis* Adherence to Oral Streptococci and Biofilm Formation Several 'second generation' click inhibitors of the multi-species biofilm propagated by the adherence of the oral pathogen *Porphyromonas gingivalis* to *Streptococcus gordonii* were synthesized and evaluated. The design of the structures was based on the results obtained with the first generation diphenyloxazole 'click' inhibitors which bear suitable hydrophobic and polar groups within a dual scaffold molecule bearing a 1,2,3-triazole spacer. The structures of the synthetic targets reported herein now consist of a triazolyl(phenylsulfonylmethyl) and a triazolyl(phenylsulfinylmethyl) spacer which joins a 4,5-diphenyloxazole with both phenyl rings bearing lipophilic substituents. The triazolyl "linker" group is formed by a click reaction between the 4-azido(phenylsulfonyl/sulfinylmethyl) oxazoles and acetylenic components having aryl groups bearing hydrophobic substituents. The 1,3,5-trisubstituted-2,4,6-triazine scaffold of the most active click compounds were modeled after the structural motif termed the VXXLL nuclear receptor (NR) box. When substituted at the 3- and 5-positions with 2- and 4-fluorophenylamino and N,N-diethylamino units, the candidates bearing the 1,3,5-trisubstituted-2,4,6-triazine scaffold formed a substantial subset of the second-generation click candidates. Several of the click products showed inhibition of the adherence of *P. gingivalis* to *S. gordonii* with an IC$_{50}$ range of 2.3-5.3 µM.

1. Introduction

In the human oral cavity, a consortium of anaerobic bacteria including *Porphyromonas gingivalis, Tannerella forsythsis* and *Treponema denticola* colonizes the subgingival pocket and has been designated as the 'red complex' that is strongly associated with chronic adult periodontitis [1]. *P. gingivalis* is considered a key periodontal pathogen that may function to shape the overall microbial community leading to dysbiosis and tissue damage [2-5]. Current methods to treat periodontitis involves scaling, root planing and surgery may be required to reduce subgingival pocket depth in more severe cases. Therapeutic approaches that specifically target periodontal pathogens like *P. gingivalis* are lacking. In addition, therapies that prevent or limit re-colonization of the oral cavity by *P. gingivalis* after treatment procedures are not available. Although the primary niche for *P. gingivalis* is a mixed community of bacterial species in the subgingival pocket, upon initial entry into the oral cavity it first colonizes supragingival plaque [6] the interaction of *P. gingivalis* with oral streptococci is important for this early colonization event [7,8]. Thus, adherence of *P. gingivalis* with commensal streptococci represents an ideal point for therapeutic intervention to control colonization (or re-colonization) of the oral cavity by *P. gingivalis*. Adherence to streptococci is mediated by a protein-protein interaction that occurs between the minor fimbrial antigen (Mfa) of *P. gingivalis* and the antigen I/II (Ag I/II) polypeptide of streptococci [9-11]. Daep et al. identified a discrete domain in Ag I/II protein that is required for interaction with Mfa and showed that this region resembles the eukaryotic nuclear receptor (NR) box protein-protein interaction domain [9,10]. Daep et al. also showed that the NR box is comprised of two functional peptide motifs, VXXLL and NITVK, and a synthetic peptide encompassing both motifs functioned as a potent inhibitor of *P. gingivalis* adherence to streptococci and significantly reduced *P. gingivalis* virulence in vivo [11]. These studies suggested that *P. gingivalis* colonization of the oral cavity can be controlled by preventing its initial association with streptococci and that inhibitors of the Mfa-AgI/II interaction may represent potential therapeutic agents to control periodontal disease. However, the use of peptides as therapeutic agents has limitations arising from the relatively high cost of peptide synthesis and their susceptibility to degradation by proteases expressed by oral organisms, including *P. gingivalis* itself.

The development of small-molecule peptidomimetics is one approach to generate hydrolytically-stable inhibitory analogues of the inhibitory peptide and at a decreased cost of synthesis. To this end, we previously reported the synthesis and testing of small molecule inhibitors based on a non-peptide backbone that mimic the natural peptide substrate recognized by Mfa [12, 13]. A 2,4,5-trisubstituted oxazole framework was utilized to mimic the NITVK motif and mono-, di- and tri-substituted aryl rings having hydrophobic substituents represented VXXLL mimics. These two synthetic small-molecule scaffolds were subsequently joined via the 'click' reaction [14-22]. In this report, we describe the syntheses and click reactions of similar 2,4,5-trisubstituted oxazole NITVK-mimics[23-26]. These reacting components are now used in conjunction with a sulfinylaryl- and sulfonylaryl-1,2,3-triazole linkers, albeit with the mono- and di-substituted aryl groups acting as the VXXLL structural mimic. Similar to the previous 'first generation' compounds, the newly-formed 1,2,3-triazole linker arising from the click reaction functions as the polar, slightly basic section of the entire peptidomimetic with the phenylsulfinyl or phenylsulfonyl portion allowing several more degrees of conformational freedom in the molecule's overall topology. These second generation compounds are divided into three groups based on the linker motifs joining the two scaffolds, the substitutions on the phenyl rings of the 4,5-diaryloxazole, the hydrophobic substituents on the distal (VXXLL) aryl ring and those in which the 3,5-(arylamino)-substituted 2,4,6-triazine unit represents the distal VXXLL locus (FIG. 1). Further, the 2,4,6-triazines all bear hydrophobic substituents such as 2- and 4- fluorophenylamino and required installation of the acetylenic component so that the resulting 6-acetylenic-2,4-di-N-substituted 1,3,5-triazines could react with the NITVK-mimic co-reactant azides in the click reaction.

2. Results and Discussion

2.1 Design and Chemistry

Our approach toward the design of the second generation inhibitors is modeled after the previously-reported individual VXXLL and NITVK-peptidomimetic motifs which encompasses both the trisubstituted oxazole (NITVK) and mono- and disubstituted aryl (VXXLL) segments of the original inhibitory polypeptide designed in these laboratories [12]. The separate motifs were each functionalized with azide and acetylene reactant groups to facilitate the formation of the "click" triazole linker which provided the completed scaffold (Scheme 1).

Scheme 1. General azide/alkyne scaffold construction of second generation inhibitors via a 'click' reaction. The entire linker modality is a sulfinyl- or sufonylphenyltriazole.

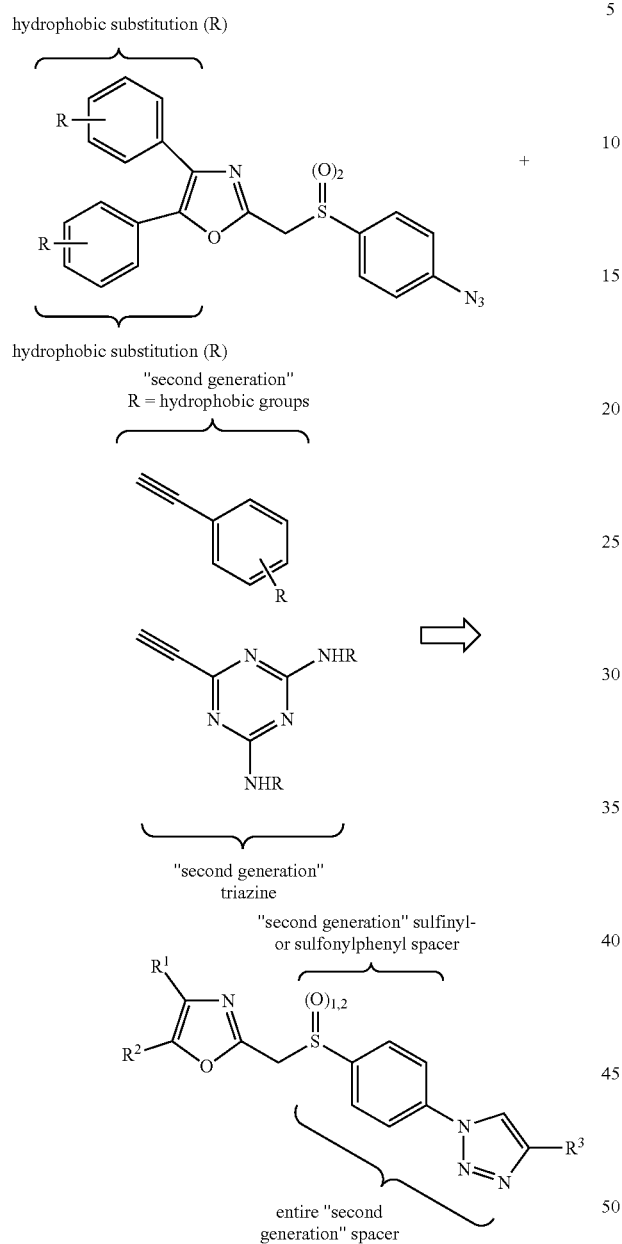

TABLE 1

Aryl alkynyl click partners 16-27.[a]

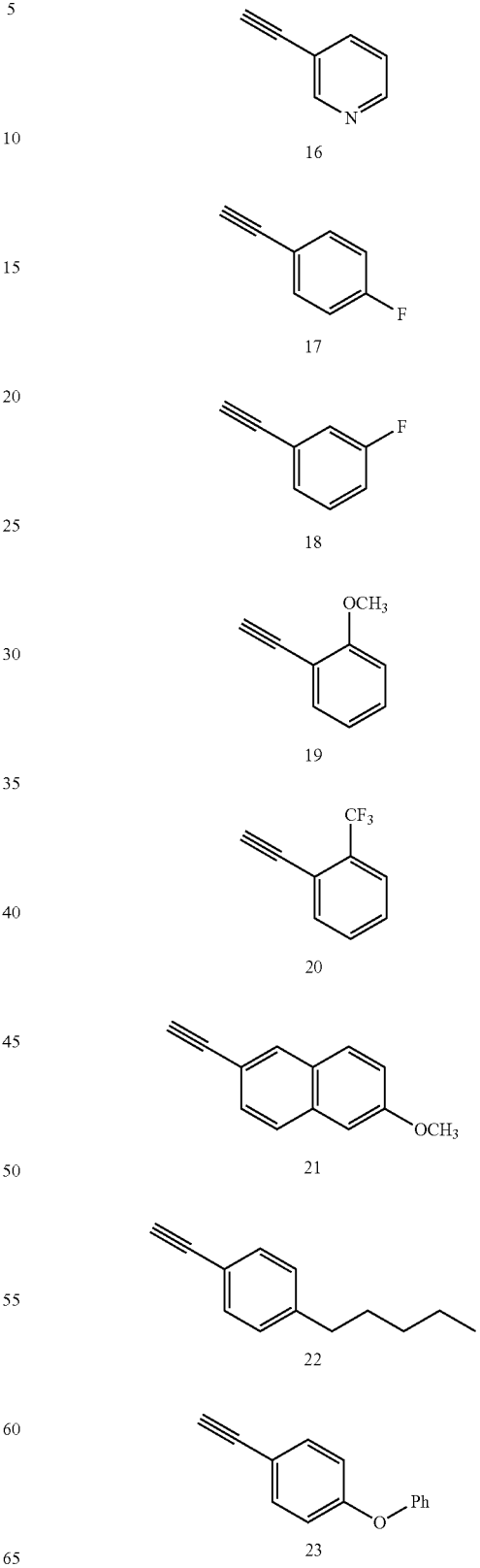

Within the substituted aryl groups of the VXXLL segment bearing acetylenic reacting components (Table 1), is the subgroup of meta-disposed trisubstituted triazines which bear two fluorophenylaminogroups. We chose a sulfinyl/sulfonyl group in tandem with a para-substituted azidophenyl group to now provide an extended linker which should have unique interaction properties. There is a dual character of the weakly polar sulfonyl group as a hydrogen bond acceptor and as a hydrophobic group [27]. Furthermore, the sulfonyl group is capable of forming van der Waals interactions with nonpolar atoms together with weak hydrogen bonds with hydrogens α-to electron-withdrawing groups. A very similar issue characterizes the sulfinyl group whereby the sulfoxide (S=O) itself is also a very weak hydrogen bond acceptor [28].

TABLE 1-continued

Aryl alkynyl click partners 16-27.[a]

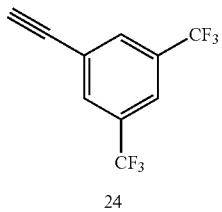 [SMILES: C#Cc1cc(C(F)(F)F)cc(C(F)(F)F)c1]

24

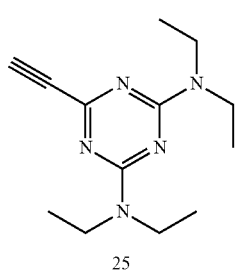 [SMILES: C#Cc1nc(N(CC)CC)nc(N(CC)CC)n1]

25

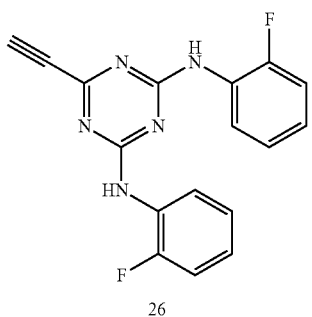 [SMILES: C#Cc1nc(Nc2ccccc2F)nc(Nc2ccccc2F)n1]

26

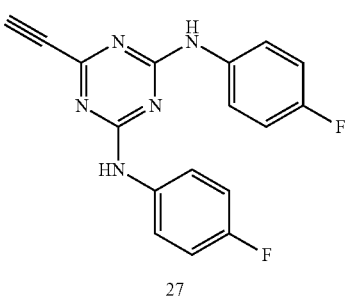 [SMILES: C#Cc1nc(Nc2ccc(F)cc2)nc(Nc2ccc(F)cc2)n1]

27

[a]Arranged in order of increasing molecular weight

The initial group (Group I) of sulfoxide and sulfone click products (28-45, Table 2) that were prepared and underwent evaluation, were derived from both the unsubstituted diphenyloxazole scaffolds 10, 13 (Scheme 2) and the complete array of mono-, di and trisubstituted arylacetylene units from Table 1.

TABLE 2

Click reactions of azidophenylsulfoxides 10 and azidophenylsulfones 13 with selected arylacetylenes 16-24 to give Group I triazoles 28-45.

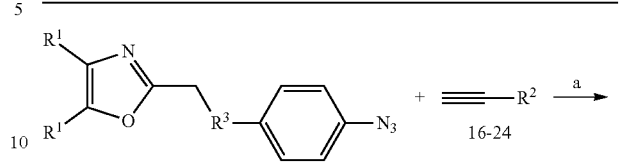

10, $R^1$, $R^2$ = Ph, $R^3$ = SO
13, $R^1$, $R^2$ = Ph, $R^3$ = $SO_2$

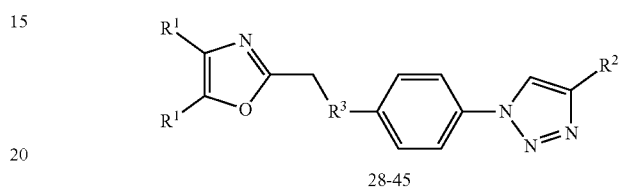

28-45

| Compound (Yield %)[b] | IC$_{50}$ (μM) |
|---|---|
| 28, $R^1$, $R^1$ = Ph, $R^2$ = 3-pyridyl, $R^3$ = SO (46) | >60.0 |
| 29, $R^1$, $R^1$ = Ph, $R^2$ = 4-fluorophenyl, $R^3$ = SO (86) | >60.0 |
| 30, $R^1$, $R^1$ = Ph, $R^2$ = 3-fluorophenyl, $R^3$ = SO (97) | 47.3 |
| 31, $R^1$, $R^1$ = Ph, $R^2$ = 2-methoxyphenyl, $R^3$ = SO (95) | >60.0 |
| 32, $R^1$, $R^1$ = Ph, $R^2$ = 2-(trifluoromethyl)phenyl, $R^3$ = SO (60) | >60.0 |
| 33, $R^1$, $R^1$ = Ph, $R^2$ = 6-methoxynaphthalene-2-yl, $R^3$ = SO (58) | >60.0 |
| 34, $R^1$, $R^1$ = Ph, $R^2$ = 4-(n-pentyl)phenyl, $R^3$ = SO (39) | >60.0 |
| 35, $R^1$, $R^1$ = Ph, $R^2$ = 4-(phenoxy)phenyl, $R^3$ = SO (79) | >60.0 |
| 36, $R^1$, $R^1$ = Ph, $R^2$ = 3,5-Di-(trifluoromethyl)phenyl, $R^3$ = SO (89) | >60.0 |
| 37, $R^1$, $R^1$ = Ph, $R^2$ = 3-pyridyl, $R^3$ = $SO_2$ (73) | >60.0 |
| 38, $R^1$, $R^1$ = Ph, $R^2$ = 4-fluorophenyl, $R^3$ = $SO_2$ (63) | 15.7 |
| 39, $R^1$, $R^1$ = Ph, $R^2$ = 3-fluorophenyl, $R^3$ = $SO_2$ (69) | 33.6 |
| 40, $R^1$, $R^1$ = Ph, $R^2$ = 2-methoxyphenyl, $R^3$ = $SO_2$ (98) | 13.1 |
| 41, $R^1$, $R^1$ = Ph, $R^2$ = 2-(trifluoromethyl)phenyl, $R^3$ = $SO_2$ (54) | >60.0 |
| 42, $R^1$, $R^1$ = Ph, $R^2$ = 6-methoxynaphthalene-2-yl, $R^3$ = $SO_2$ (97) | >60.00 |
| 43, $R^1$, $R^1$ = Ph, $R^2$ = 4-(n-pentyl)phenyl, $R^3$ = $SO_2$ (77) | 36.6 |
| 44, $R^1$, $R^1$ = Ph, $R^2$ = 4-(phenoxy)phenyl, $R^3$ = $SO_2$ (97) | 16.5 |
| 45, $R^1$, $R^1$ = Ph, $R^2$ = 3,5-Di-(trifluoromethyl)phenyl, $R^3$ = $SO_2$ (63) | 38.5 |

[a]Reagents/Conditions: $CuSO_4 \cdot 5H_2O$/Na ascorbate/THF-$H_2O$ (2:1).
[b]Yields are for isolated pure compounds 2-Substituted-4,5-diphenyloxazole azide units containing the 4,5-di-(4-chlorophenyl)- and 4,5-di-(4-fluorophenyl) groups (11, 14 and 12, 15, Scheme 3), as reported previously, offered hydrophobic interactions at both aryl positions in the NITVK-trisubstituted oxazole-associated locus and comprised the next group (Group II) of triazole-linked phenyl sulfoxides and sulfones. When azides 11, 12, 14 and 15 were reacted with acetylenes 17-19, these click products carried the complete array of halogenated (F, Cl) substituents on both the arylrings of the 4,5-diaryloxazole (NITVK) and the aryltriazole-(VXXLL) loci (46-57, Table 3). Our third group

TABLE 3

Click reactions of halogenated azidomethylsulfoxides 11, 12 and azidophenylsulfones 14, 15 with selected arylacetylenes 17, 18, 19 to give Group II click products 46-57.

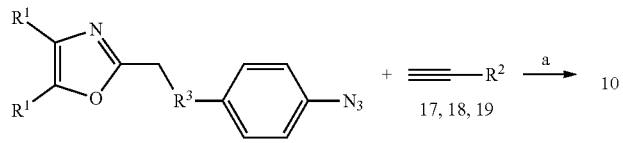

11, $R^1$, $R^1$ = 4-fluorophenyl, $R^3$ = SO
12, $R^1$, $R^1$ = 4-chlorophenyl, $R^3$ = SO
14, $R^1$, $R^1$ = 4-fluorophenyl, $R^3$ = $SO_2$
15, $R^1$, $R^1$ = 4-chlorophenyl, $R^3$ = $SO_2$

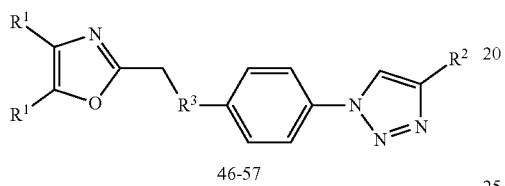

46-57

| Compound (Yield %)[b] | $IC_{50}$ (μM) |
|---|---|
| 46, $R^1$, $R^1$ = 4-fluorophenyl, $R^2$ = 3-fluorophenyl, $R^3$ = SO (78) | 5.30 |
| 47, $R^1$, $R^1$ = 4-fluorophenyl, $R^2$ = 4-fluorophenyl, $R^3$ = SO (83) | 35.9 |
| 48, $R^1$, $R^1$ = 4-fluorophenyl, $R^2$ = 2-methoxypheny, $R^3$ = SO (92) | 7.20 |
| 49, $R^1$, $R^1$ = 4-chlororophenyl, $R^2$ = 3-fluorophenyl, $R^3$ = SO (52) | 15.1 |
| 50, $R^1$, $R^1$ = 4-chlorophenyl, $R^2$ = 4-fluorophenyl, $R^3$ = SO (93) | 39.8 |
| 51, $R^1$, $R^1$ = 4-chlorophenyl, $R^2$ = 2-methoxyphenyl, $R^3$ = SO (76) | 10.2 |
| 52, $R^1$, $R^1$ = 4-fluorophenyl, $R^2$ = 3-fluorophenyl, $R^3$ = $SO_2$ (79) | 40.0 |
| 53, $R^1$, $R^1$ = 4-fluorophenyl, $R^2$ = 4-fluorophenyl, $R^3$ = $SO_2$ (83) | 40.0 |
| 54, $R^1$, $R^1$ = 4-fluorophenyl, $R^2$ = 2-methoxyphenyl, $R^3$ = $SO_2$ (95) | 21.2 |
| 55, $R^1$, $R^1$ = 4-chlororophenyl, $R^2$ = 3-fluorophenyl, $R^3$ = $SO_2$ (84) | 18.2 |
| 56, $R^1$, $R^1$ = 4-chlorophenyl, $R^2$ = 4-fluorophenyl, $R^3$ = $SO_2$ (93) | 6.30 |
| 57, $R^1$, $R^1$ = 4-chlorophenyl, $R^2$ = 2-methoxyphenyl, $R^3$ = $SO_2$ (81) | 20.0 |

[a] Reagents/Conditions: $CuSO_4 \cdot 5H_2O$/Na ascorbate/THF-$H_2O$ (2:1).
[b] Yields are for isolated pure compounds (Group III) of second-generation inhibitors include a more varied array of the VXXLL sectors (90-124, Table 4) which are based on the 1,3,5-trisubstituted-2,4,6-triazine motif put forth by Katzenellenbogen and others [29-31] in their work on mimicking helical peptide NR boxes containing suitably-juxtaposed leucine residues. Thus, the acetylenic triazine click partners (25-27, Table 1) used for Group III are constructs that have the moderately hydrophobic

TABLE 4

Click reactions of azides 73-87 with acetylenes 25, 26, 27 to give Group III triazole products 90-124.

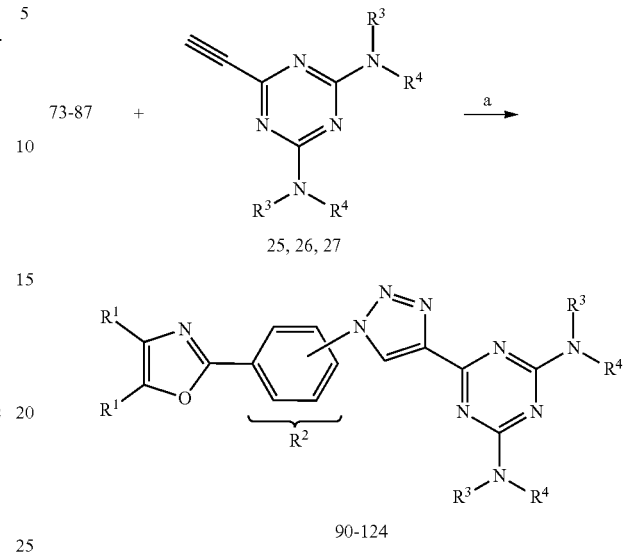

90-124

| Compound (Yield %)[b] | $IC_{50}$ (μM) |
|---|---|
| 90, $R^1$ = phenyl, $R^2$ = 3-triazolyl, $R^3$, $R^4$ = ethyl (76) | 20.7 |
| 91, $R^1$ = phenyl, $R^2$ = 4-triazolyl, $R^3$, $R^4$ = ethyl (90) | >60.0 |
| 92, $R^1$ = 4-fluorophenyl, $R^2$ = 3-triazolyl, $R^3$, $R^4$ = ethyl (48) | >60.0 |
| 93, $R^1$ = 4-fluorophenyl, $R^2$ = 4-triazolyl, $R^3$, $R^4$ = ethyl (45) | 9.40 |
| 94, $R^1$ = 4-chlorophenyl, $R^2$ = 3-triazolyl, $R^3$, $R^4$ = ethyl (52) | 16.0 |
| 95, $R^1$ = 4-chlorophenyl, $R^2$ = 4-triazolyl, $R^3$, $R^4$ = ethyl (57) | 3.70 |
| 96, $R^1$ = 4-methoxyphenyl, $R^2$ = 3-triazolyl, $R^3$, $R^4$ = ethyl (53) | >60.0 |
| 97, $R^1$ = 4-methoxyphenyl, $R^2$ = 4-triazolyl, $R^3$, $R^4$ = ethyl (63) | 36.6 |
| 98, $R^1$ = 2-furyl, $R^2$ = 3-triazolyl, $R^3$, $R^4$ = ethyl (52) | >60.0 |
| 99, $R^1$ = 2-furyl, $R^2$ = 4-triazolyl, $R^3$, $R^4$ = ethyl (46) | >60.0 |
| 100, $R^1$ = phenyl, $R^2$ = 3-triazolyl, $R^3$ = 2-fluorophenyl, $R^4$ = H (80) | 9.6.0 |
| 101, $R^1$ = phenyl, $R^2$ = 4-triazolyl, $R^3$ = 2-fluorophenyl, $R^4$ = H (65) | >60.0 |
| 102, $R^1$ = 4-fluorophenyl, $R^2$ = 3-triazolyl, $R^3$ = 2-fluorophenyl, $R^4$ = H (95) | 5.00 |
| 103, $R^1$ = 4-fluorophenyl, $R^2$ = 4-triazolyl, $R^3$ = 2-fluorophenyl, $R^4$ = H (77) | 12.3 |
| 104, $R^1$ = 4-chlorophenyl, $R^2$ = 3-triazolyl, $R^3$ = 2-fluorophenyl, $R^4$ = H (70) | 33.8 |
| 105, $R^1$ = 4-chlorophenyl, $R^2$ = 4-triazolyl, $R^3$ = 2-fluorophenyl, $R^4$ = H (69) | >60.0 |
| 106, $R^1$ = 4-methoxyphenyl, $R^2$ = 3-triazolyl, $R^3$ = 2-fluorophenyl, $R^4$ = H (66) | >60.0 |
| 107, $R^1$ = 4-methoxyphenyl, $R^2$ = 4-triazolyl, $R^3$ = 2-fluorophenyl, $R^4$ = H (75) | 40.0 |
| 108, $R^1$ = 2-furyl, $R^2$ = 3-triazolyl, $R^3$ = 2-fluorophenyl, $R^4$ = H (69) | >60.0 |
| 109, $R^1$ = 2-furyl, $R^2$ = 4-triazolyl, $R^3$ = 2-fluorophenyl, $R^4$ = H (83) | >60.0 |
| 110, $R^1$ = phenyl, $R^2$ = 2-triazolyl, $R^3$ = 4-fluorophenyl, $R^4$ = H (30) | >60.0 |
| 111, $R^1$ = phenyl, $R^2$ = 3-triazolyl, $R^3$ = 4-fluorophenyl, $R^4$ = H (82) | 4.30 |
| 112, $R^1$ = phenyl, $R^2$ = 4-triazolyl, $R^3$ = 4-fluorophenyl, $R^4$ = H (48) | >60.0 |
| 113, $R^1$ = 4-fluorophenyl, $R^2$ = 2-triazolyl, $R^3$ = 4-fluorophenyl, $R^4$ = H (77) | 49.2 |
| 114, $R^1$ = 4-fluorophenyl, $R^2$ = 3-triazolyl, $R^3$ = 4-fluorophenyl, $R^4$ = H (87) | >60.0 |
| 115, $R^1$ = 4-fluorophenyl, $R^2$ = 4-triazolyl, | 2.30 |

TABLE 4-continued

Click reactions of azides 73-87 with acetylenes 25, 26, 27 to give Group III triazole products 90-124.

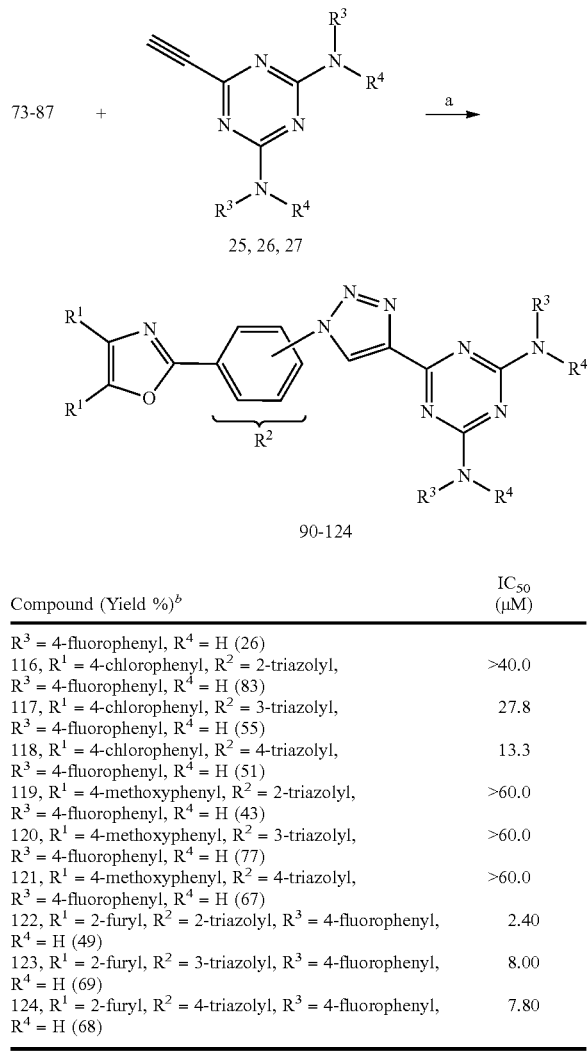

| Compound (Yield %)[b] | IC$_{50}$ (µM) |
|---|---|
| R$^3$ = 4-fluorophenyl, R$^4$ = H (26) | |
| 116, R$^1$ = 4-chlorophenyl, R$^2$ = 2-triazolyl, R$^3$ = 4-fluorophenyl, R$^4$ = H (83) | >40.0 |
| 117, R$^1$ = 4-chlorophenyl, R$^2$ = 3-triazolyl, R$^3$ = 4-fluorophenyl, R$^4$ = H (55) | 27.8 |
| 118, R$^1$ = 4-chlorophenyl, R$^2$ = 4-triazolyl, R$^3$ = 4-fluorophenyl, R$^4$ = H (51) | 13.3 |
| 119, R$^1$ = 4-methoxyphenyl, R$^2$ = 2-triazolyl, R$^3$ = 4-fluorophenyl, R$^4$ = H (43) | >60.0 |
| 120, R$^1$ = 4-methoxyphenyl, R$^2$ = 3-triazolyl, R$^3$ = 4-fluorophenyl, R$^4$ = H (77) | >60.0 |
| 121, R$^1$ = 4-methoxyphenyl, R$^2$ = 4-triazolyl, R$^3$ = 4-fluorophenyl, R$^4$ = H (67) | >60.0 |
| 122, R$^1$ = 2-furyl, R$^2$ = 2-triazolyl, R$^3$ = 4-fluorophenyl, R$^4$ = H (49) | 2.40 |
| 123, R$^1$ = 2-furyl, R$^2$ = 3-triazolyl, R$^3$ = 4-fluorophenyl, R$^4$ = H (69) | 8.00 |
| 124, R$^1$ = 2-furyl, R$^2$ = 4-triazolyl, R$^3$ = 4-fluorophenyl, R$^4$ = H (68) | 7.80 |

[a]Conditions/Reagents: CuSO$_4$·5H$_2$O/Na ascorbate/THF-H$_2$O (2:1).
[b]Yields are for isolated pure compounds.

dialkylamino as well as the highly hydrophobic fluorophenylamino groups at positions 3 and 5 of the 2,4,6-triazine [32-35]. Furthermore, the utilization of halogens and halogen isosteres as substituents on the aryl rings of the NITVK/oxazole framework has been commented on in our previous in vitro and in vivo studies [12,13], and as a result we decided on the array of azide coupling partners bearing halogenated and methoxy substitution 73-87 (Scheme 4) to be coupled with the acetylenic triazines 25-27. Included with our Group III candidates are a new set of compounds 98, 99, 108, 109, 122-124 (Table 4) where the both phenyl rings at the 4,5-positions of the oxazole were substituted with furan rings. Replacement of benzene with furan is not an uncommon example of effective bioisosteric replacement in medicinal chemistry [36]. The furan system is π-electron rich, but also carries a mild hydrogen-bonding component along with its aromatic structure. The oxazole and triazole motifs in the backbone of our peptidomimetic inhibitor candidates offer rigidity as well as the potential for hydrogen bonding. Since the introduction of click chemistry, the 1,2,3-triazole has been effectively deployed as an easily-formed peptide bond isostere thereby linking complex polypeptides as well as sectors of less complex peptidomimetics [37,38]. A similar case is made for the oxazole/NITVK scaffold whereby its conferred rigidity influences the disposition of the distal 4,5-(halogenated) diphenyl residues [39]. Our inhibitor synthesis begins with the preparation of the individual azide and acetylene click reacting partners (Schemes 2, 3, 4). 2-Chloromethyl-4,5-diphenyloxazoles 1-3, versatile synthetic intermediates prepared in multi-gram quantities and in modest to good yields by methods previously reported from these laboratories, are the starting points (Scheme 2) [23-36]. The chloromethyl oxazoles 1-3 are reacted with 4-aminothiophenol in the presence of sodium hydride (THF) to afford the 4-(aminothiophenyl) oxazoles 4-6 in yields ranging from 66 to 85%.

Scheme 2. Synthesis of Azidophenylsulfinyl and Azidophenylsulfonyl Click Partners (10-15)

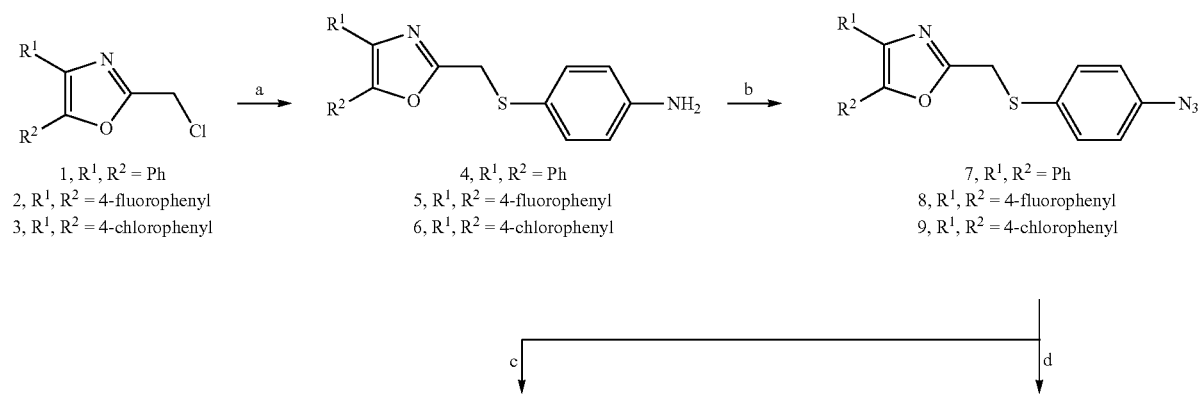

1, R$^1$, R$^2$ = Ph
2, R$^1$, R$^2$ = 4-fluorophenyl
3, R$^1$, R$^2$ = 4-chlorophenyl 4, R$^1$, R$^2$ = Ph
5, R$^1$, R$^2$ = 4-fluorophenyl
6, R$^1$, R$^2$ = 4-chlorophenyl 7, R$^1$, R$^2$ = Ph
8, R$^1$, R$^2$ = 4-fluorophenyl
9, R$^1$, R$^2$ = 4-chlorophenyl -continued

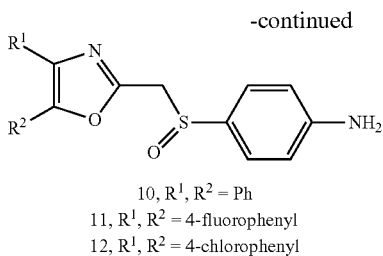

10, R¹, R² = Ph
11, R¹, R² = 4-fluorophenyl
12, R¹, R² = 4-chlorophenyl

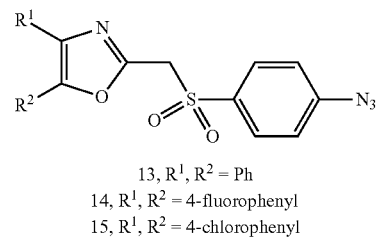

13, R¹, R² = Ph
14, R¹, R² = 4-fluorophenyl
15, R¹, R² = 4-chlorophenyl

Reagents/Condtions: (a) NaH/4-aminothiophenol/THF/0-5° C. to rt/16 h (66-85%). (b) NaNO₂/10% HCl/NaN₃/0-5° C. to rt/16 h (61-98%). (c) MCPBA (1-2 eq)/DCM/rt/16 h (86-95%). (d) MCPBA (3 eq)/DCM/rt/16 h (86-93%).

Treatment of the (aminothiophenyl) oxazoles 4-6 with sodium nitrite in 10% aqueous HCl and sodium azide (5° C. to rt, 16 h) gave the corresponding 4-azidophenyl(oxazolyl) sulfides 7-9 (61-98%) with no interference from the sulfide group. Oxidation of the sulfide moiety of 7-9 could provide either the corresponding sulfoxides 10-12 or the corresponding sulfones 13-15 depending on the equivalents of oxidant employed. Thus, treatment of the sulfides 7-9 with m-chloroperbenzoic acid (1.2 equivalents) in dichloromethane (16 h, rt) gave the corresponding sulfoxides 10-12 (86-95%), while treating 7-9 with three equivalents of the oxidant provided the corresponding sulfones 13-15 (86-93%) in excellent yield. Both the oxidations of the sulfides to the sulfoxides and sulfones were optimized and these compounds were obtained as crystalline solids which were easily purified by column chromatography on silica gel. Interestingly, ¹H NMR spectra revealed a distinct non-equivalence between the enantiotopic methylene protons at the 2-position of the oxazole ring in sulfoxides 10-12, while the same set of protons in the corresponding sulfones 13-15 were equivalent. Using the percarboxylic acid oxidation protocol, the sulfoxide products are presumed to be racemic at sulfur, and were bioassayed as the racemic mixtures. The click reactions of azidophenylsulfoxides 10-12 and azidophenylsulfones 13-15 with the acetylenic partners 16-24 (Table 1) to give the click triazole products 28-45 (Table 2) were conducted under standard conditions (CuSO₄/sodium ascorbate/THF/H₂O) developed in these laboratories for our previously-reported candidates. The 4,5-bis (4-fluorophenyl) oxazole sulfoxide 11 and the 4,5-bis (fluorophenyl) oxazole sulfone 14 together with the corresponding bis-(4-chlorophenyl) sulfoxide and sulfone 12, 15 (Scheme 2) were reacted with arylacetylenes 17, 18, 19 to afford the sulfinyl and sulfonyl-linked triazole click products 46-57 in yields ranging from 52 to 93% (Table 3). The click reactions between azides 11, 12, 14 and 15 and the group of arylacetylenes 17, 18, 19 were conducted under the same conditions as those detailed on Table 2. The acetylenic triazine click partners 25-27 which comprised the VXXLL scaffold portion of click products 90-124 (Table 4) were prepared from 2,4,6-trichloro-1,3,5-triazine (cyanuric chloride) (Scheme 3). Lithioethynyltrimethylsilane, formed from ethynyltrimethyl-silane Scheme 3. Synthesis of the Acetylenic Triazine Click Partners 25, 26, 27.

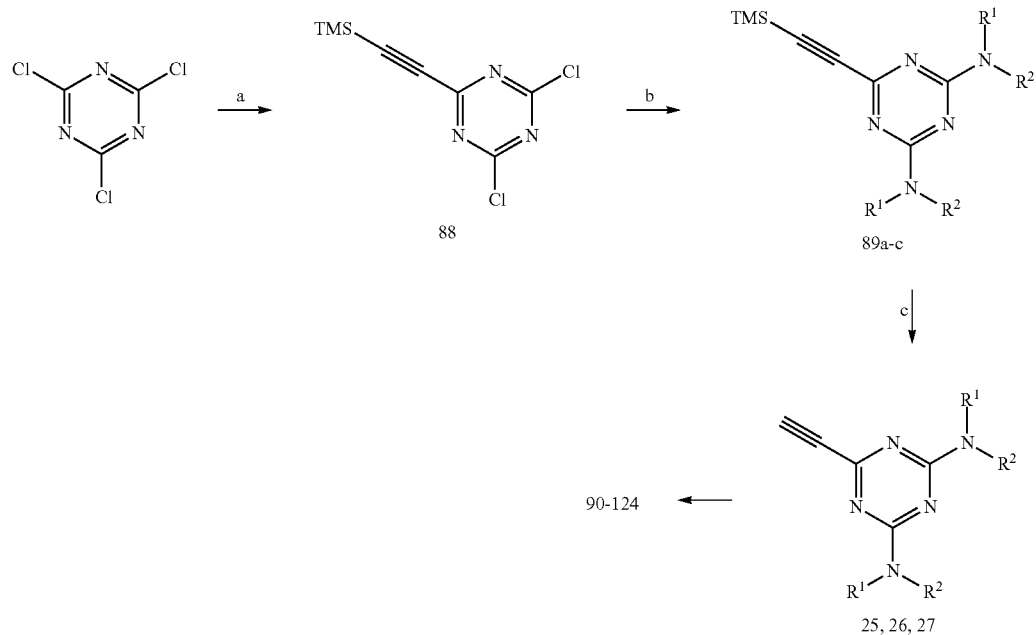

Reagents/Conditions: (a) ethynyltrimethylsilane/n-BuLi/THF/0° C./1 h; (b) 4-fluoroaniline, 2-fluoroaniline or diethylamine/THF/0° C., to rt/16 h. (c) TBAF/THF/0° C. to rt/2 h.

and n-butyllithium (THF/O-5° C.), was added to cyanuric chloride to give 2-(3,5-dichlorophenyl) ethynyltrimethylsilane 88 (0° C.→rt/3 h). Direct addition of excess amine (diethylamine, 2-fluoroaniline or 4-fluoroaniline) to 88 followed by stirring (0° C.→rt/16 h) gave the TMS-acetylenic 3,5-diamino triazines 89a-c which were purified by column chromatography. Removal of the trimethylsilylgroup was accomplished with tetra-n-butylammonium fluoride (TBAF/THF/0° C.→rt) which afforded the acetylenic triazines 25-27. The preparation of the azidophenyloxazole-based click partners 73-87 which were reacted with the acetylenic triazines 25-27 is detailed in Scheme 4. The appropriate benzoin, where Scheme 4. Synthesis of 2-(2-azidophenyl)-, 2-(3-azidophenyl)- and 2(4-azidophenyl)-4,5-diaryloxazole click partners 73-87 through benzoin esters 58-72.

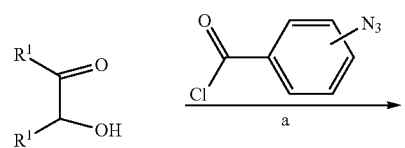

$R^1$ = phenyl
$R^1$ = 4-fluorophenyl
$R^1$ = 4-chlorophenyl
$R^1$ = 4-methoxyphenyl
$R^1$ = 2-furyl

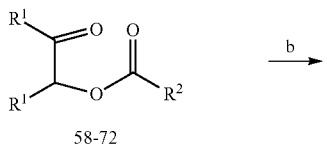

58-72

58, $R^1$ = phenyl, $R^2$ = 2-azidophenyl (82)
59, $R^1$ = phenyl, $R^2$ = 3-azidophenyl (89)
60, $R^1$ = phenyl, $R^2$ = 4-azidophenyl (98)
61, $R^1$ = 4-chlorophenyl, $R^2$ = 2-azidophenyl (29)
62, $R^1$ = 4-chlorophenyl, $R^2$ = 3-azidophenyl (74)
63, $R^1$ = 4-chlorophenyl, $R^2$ = 4-azidophenyl (99)
64, $R^1$ = 4-fluorophenyl, $R^2$ = 2-azidophenyl (93)
65, $R^1$ = 4-fluorophenyl, $R^2$ = 3-azidophenyl (99)
66, $R^1$ = 4-fluorophenyl, $R^2$ = 4-azidophenyl (84)
67, $R^1$ = 4-methoxyphenyl, $R^2$ = 2-azidophenyl (98)
68, $R^1$ = 4-methoxyphenyl, $R^2$ = 3-azidophenyl (83)
69, $R^1$ = 4-methoxyphenyl, $R^2$ = 4-azidophenyl (93)
70, $R^1$ = 2-furyl, $R^2$ = 2-azidophenyl (78)
71, $R^1$ = 2-furyl, $R^2$ = 3-azidophenyl (84)
72, $R^1$ = 2-furyl, $R^2$ = 4-azidophenyl (75)

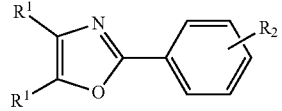

73-87

73, $R^1$ = phenyl, $R^2$ = 2-azido (42)
74, $R^1$ = phenyl, $R^2$ = 3-azido (83)
75, $R^1$ = phenyl, $R^2$ = 4-azido (94)
76, $R^1$ = 4-chlorophenyl, $R^2$ = 2-azido (47)
77, $R^1$ = 4-chlorophenyl, $R^2$ = 3-azido (92)
78, $R^1$ = 4-chlorophenyl, $R^2$ = 4-azido (69)
79, $R^1$ = 4-fluorophenyl, $R^2$ = 2-azido (71)
80, $R^1$ = 4-fluorophenyl, $R^2$ = 3-azido (59)
81, $R^1$ = 4-fluorophenyl, $R^2$ = 4-azido (67)
82, $R^1$ = 4-methoxyphenyl, $R^2$ = 2-azido (60)
83, $R^1$ = 4-methoxyphenyl, $R^2$ = 3-azido (63)
84, $R^1$ = 4-methoxyphenyl, $R^2$ = 4-azido (65)
85, $R^1$ = 2-furyl, $R^2$ = 2-azido (13)
86, $R^1$ = 2-furyl, $R^2$ = 3-azido (19)
87, $R^1$ = 2-furyl, $R^2$ = 4-azido (19)
Reagents/Conditions: (a) DMAP/DCM/16 h. (b) NH$_4$OAc/HOAc/115-120° C./3-4 h.

$R^1$=phenyl, 4-fluorophenyl, 4-chlorophenyl, 4-methoxyphenyl or 2-furyl, was reacted with 2-azido, 3-azido- or 4-azidobenzoyl chloride in the presence of 4-dimethylaminopyridine to give the corresponding benzoin esters 58-72. The yields ranged from 29-99% after purification by column chromatography on silica gel. Cyclization of the benzoin esters 58-72 to the corresponding 4,5-diaryl-2-azidophenyloxazoles 73-87 was accomplished by heating the benzoin esters with ammonium acetate in acetic acid (115-120° C.). The 4,5-diaryloxazoles 73-87 having 2-azidophenyl, 3-azidophenyl or 4-azidophenyl substituents at the 2-position of the oxazole ring were purified by silica gel column chromatography, and provided crystalline products in yields ranging from 13 to 94% with the cyclizations of the 2-furyl esters giving the lowest yields. The click reactions of azides 73-87 with the arylacetylenic substrates 25-27 were conducted using a copper (II) sulfate/sodium ascorbate protocol with tetrahydrofuran/water as a solvent system and afforded the corresponding 4,5-diaryloxazolyl-1,2,3-triazoles 90-124 with the expected regiochemistry (Table 4). The regiochemistry of the dipolar cycloaddition 'click' reaction affords products in which the substitution could be 1,4- or 1,5- on the triazole ring depending on the reagents and the conditions used. All of the click products described herein (Tables 2, 3 and 4) were formed as a result of copper (I) catalysis which gave exclusively the 1,4- or "anti"-substituted 1,2,3-triazole [21].

2.2 Bioassay Results and Discussion

To assess the functional activity of the click products, compounds 28-57 (Groups I and II) and 90-124 (Group III) were examined for inhibition of *P. gingivalis* adherence to *S. gordonii* using an established biofilm model system as described in the Section 4.2.1 [41]. A representative dose response series of inhibition of *P. gingivalis* adherence for compound 102 is shown in FIG. 2. For each compound tested, an IC$_{50}$ value for adherence inhibition was approximated after quantifying the ratio of green to red fluorescence and these values are shown in Tables 2, 3 and 4. Compounds were classified as strong (IC$_{50}$<10 µM), moderate (IC$_{50}$=10-20 µM) or weak (IC$_{50}$>20 µM) inhibitors of adherence. Twelve compounds were identified as strong inhibitors and an additional ten compounds were classified as moderate inhibitors. The most potent of these exhibited $IC_{50}$ values that were approximately 2.5-fold lower that the most potent of the previously-reported generation 1 compounds [12,13]. Compounds 54, 56, 93, 95, 100, 102, 103, and 115 were also tested to determine if they affect the growth of *P. gingivalis* or *S. gordonii*. No effect on growth of planktonic cultures was observed when cultures were incubated overnight in the presence of 40 µM compound (data not shown), indicating that the compounds do not function as antibiotics but rather inhibit *P. gingivalis* adherence to streptococci. In comparing and contrasting the top six compounds which exhibit the highest inhibitory activity, six (95, 102, 111, 115, 117, 46) fall in the range of 2.3-5.3 µM. Five of the compounds are listed in Table 4 (95-117, Group III) and one compound is listed in Table 3 (46, Group II). Compound 46 ($IC_{50}$, 5.3 µM) is the only candidate which possesses a sulfoxide group as part of the backbone as well as an m-fluorophenyl group on the triazole linker which mimics the VXXLL motif. Similar to two other highly active compounds 102 (5.0 µM) and 115 (2.3 µM), the NITVK-mimic sector is the 4,5-di-(4-fluorophenyl) oxazole. The sulfoxide group does impart asymmetry to the molecule; however, the mixture of enantiomers, assuming the peracid oxidation was racemic, was not separated and bioassayed. The Group III active compounds (95-117) all contain the 1,3,5-trisubstituted-2,4,6-triazine modeled after the Katzenellenbogen rendering of an active motif whereby the key leucine residues which mimicked the VXXLL receptor box lie in a triangular arrangement [36]. While the original iteration of the Katzenellenbogen VXXLL mimics were the hydrophobic 3,5-disubstituted-di-N-alkyamino-triazine motifs, we introduced the hydrophobic 2- and 4-(fluorophenyl)amino groups at positions 3 and 5 of the 2,4,6-triazine (See Compounds 102, 111, 115, 122). Compound 95 however ($IC_{50}$=3.7), contains the more closely related, nonaromatic lipid-like, diethylamino groups at positions 3 and 5 of the 2,4,6-triazine motif. The deployment of furan rings at the 4,5-positions of the oxazole in compounds 98, 99, 108, 109, 122-124 led to only one compound 122 ($IC_{50}$ 2.4 µM) of significant activity. Interestingly, along with the di-furyloxazole arrangement, candidate 122 possessed the 3,5-di-(4-fluorophenyl)aminotriazine, and was also the compound which exhibited the most bent conformation by nature of the ortho disposition of the oxazole to the triazole linker.

3. Summary

We have prepared a number of newer "second generation" click compounds which are effective inhibitors of *P. gingivalis* adherence to oral streptococci. While we noted previously that lead optimization of our first generation inhibitors could occur through adjustment/positioning of the hydrophobic groups of the mono-aryl and diaryloxazole scaffolds, we instead opted to change the nature of the linkers conjoining the two scaffolds and keep the aryl substitution constant. The new linkers comprised both sulfonyl and sulfoxide groups. Through exploring the diamino triazine motif, changes were also made to optimize the VXXLL sectors of the general inhibitor scaffold. Several of these "second-generation" compounds were shown to be more potent inhibitors of *P. gingivalis* adherence than our "first generation" compounds. As in the development of the first generation compounds, the evaluation of this new series of candidates in pertinent in vivo animal studies will be reported in due course.

4.0 Experimental Section 4.1 General Methods

Unless otherwise specified, all solvents and reagents were ACS grade and were used as supplied. Solvents were removed from reaction mixtures and extracts using standard Büchi rotary evaporators under water aspirator vacuum. Alkynes 16-24 were commercially available and were used as supplied. All melting points (mp) were determined using a Thomas-Hoover apparatus. Infrared spectra were recorded on a Perkin-Elmer Spectrum Version 10.02.00 instrument and absorptions are reported as reciprocal centimeters ($cm^{-1}$). Proton ($^{1}H$) and carbon ($^{13}C$) nmr spectra were recorded on a Varian INOVA instrument (400 MHz, 100 MHz for $^{13}C$) or a Bruker instrument at (500 MHz, 125 MHz for $^{13}C$). High resolution mass spectra (HRMS) were performed using electrospray ionization (ESI). All air and moisture-sensitive reactions were run in oven-dried glassware under an atmosphere of dry nitrogen. Gravity-column chromatography was performed on Silica Gel 60 (E. Merck, 7734, 70-230 mesh). Thin-layer chromatography (TLC) was performed with glass-backed plates (E. Merck, 5715, Silica Gel 60 $F_{254}$ 2.5 mm thickness) and visualized using 2% anisaldehyde in ethanol, 2.5% phosphomolybdic acid in ethanol or 10% sulfuric acid in ethanol.

4.1.1 Synthesis 4.1.1. General Procedure for the Synthesis of Aminophenylsulfides 4-6:

To a suspension of freshly-washed sodium hydride (1.2 equiv) in dry THF (15 mL) was added 4-aminothiophenol (1.0 equiv) under nitrogen atmosphere at 0-5° C. followed by stirring for 30 min. To this mixture was added dropwise a solution of compounds 1-3 (1.1 equiv) dissolved in THF (15 mL) at 0-5° C. After the addition was complete, the reaction temperature was gradually raised to room temperature and allowed to stir (16 h). After completion of reaction, as indicated by TLC (hexane/ethyl acetate, 3:1), the reaction mixture was quenched with cold water (25 mL). The resulting reaction mixture was extracted into dichloromethane (2×25 mL) and the organic layers were combined, dried over anhydrous sodium sulfate, filtered and evaporated. The obtained off-white crude residuee was submitted to silica gel column chromatography (hexane/ethyl acetate, 3:1) to give aminophenylsulfides 4-6 as pure off-white products.

4.1.1.1. 4-(((4,5-Diphenyloxazol-2-yl)methyl)thio)aniline (4): Light yellow solid; yield 55%; mp=131-133° C.; $R_f$=0.17 (hexane/ethyl acetate, 7:3); FT-IR: 2125, 2090, 1591, 1487, 1291 $cm^{-1}$; $^{1}H$ NMR (500 MHz, $CDCl_3$): δ7.61 (dd, J=1.5 Hz, 3.5 Hz, 2H), 7.53 (dd, J=2.0 Hz, 4.0 Hz, 2H), 7.37-7.29 (m, 8H), 6.60 (dd, J=2.0 Hz, 6.5 Hz, 2H), 4.07 (s, 2H), 3.75 (s, 2H) ppm; $^{13}C$ NMR (125 MHz, $CDCl_3$): δ160.1, 147.0, 145.8, 135.5 (overlap), 132.3, 128.5 (overlap), 128.0 (overlap), 127.9 (overlap), 126.4 (overlap), 121.2, 115.4 (overlap), 33.7 ppm; HRMS (+ESI): calcd for $[C_{22}H_{18}N_2O_5]$ 359.1218, found 359.1267 ($[M+H]^+$).

4.1.2. General Procedure for the Synthesis of Azidophenylsulfides 7-9

To a pre-chilled solution of compounds 4-6 (1.0 equiv) in aqueous HCl (4N), was added dropwise a chilled aqueous solution of sodium nitrite (1.1 equiv/10 mL/$H_2O$). The resulting yellowish reaction mixture was allowed to stir at 0-5° C. (1 h). To this clear solution, was added dropwise an aqueous solution of sodium azide (1.05 equiv/10 mL/$H_2O$) and stirring was continued (16 h) at room temperature. The progress of reaction was monitored by TLC (hexane/ethyl acetate). After completion of the reaction, the reaction mixture was extracted into dichloromethane (2×25 mL) and organic layers were combined. The organic layer was washed with saturated $NaHCO_3$ solution (30 mL), separated, dried over anhydrous sodium sulfate and filtered. Concentration of the filtrate gave the crude residue of the corresponding products which was submitted to column chromatography (hexane/ethyl acetate, 3:1) to give the pure azidophenyl sulfides 7-9.

4.1.2.1. 2-(((4-Azidophenyl)thio)methyl)-4,5-diphenyloxazole (7): Light brown solid; yield 87%; mp=64-65° C.; $R_f$=0.5 (hexane/ethyl acetate, 7.5:2.5); FT-IR: 2125, 2090, 1591, 1487, 1291 cm$^{-1}$; $^1$H NMR (400 MHz, CDCl$_3$): δ7.59 (d, J=8.0 Hz, 2H), 7.53-7.50 (m, 3H), 7.48 (s, 1H), 7.38-7.34 (m, 6H), 6.98 (d, J=8.4 Hz, 2H), 4.19 (s, 2H) ppm; $^{13}$C NMR (125 MHz, CDCl$_3$): δ159.3, 145.9, 139.6, 135.3, 133.3, 132.0, 130.4, 128.5, 128.4, 128.1, 127.8, 126.3, 119.5, 31.9 ppm; HRMS (+ESI) m/z calcd for $[C_{22}H_{16}N_4OS]^+$ 385.1123, found 385.1133 ([M+H]$^+$).

4.1.3. General Procedure for the Synthesis of Azidophenyl Sulfoxides and Sulfones 10-15:

To a clear solution of compounds 7-9 (1.0 equiv) in dichloromethane (30 mL) was added m-CPBA (1.2 equiv for synthesis of sulfoxides 10-12 and 3.0 equiv for sulfones 13-15) and the resulting solution was stirred for 16 h at room temperature. The reaction progress was monitored by TLC (hexane/ethyl acetate). After completion of the reaction, the reaction mixture was washed with saturated aqueous NaHCO$_3$ solution and the organic layer was separated and dried over anhydrous sodium sulfate. Concentration of the of organic layer provided an off-white residue of the corresponding sulfoxides and sulfones which were submitted to column chromatography (hexane/ethyl acetate) to afford the pure azidophenyl sulfoxides and sulfones 10-15.

4.1.3.1. 2-(((4-Azidophenyl)sulfinyl)methyl)-4,5-diphenyloxazole (10): Colorless oil; yield 86%; $R_f$=0.1 (ethyl acetate/hexane, 1:3); FT-IR: 3055, 2125, 2090, 1586, 1051 cm$^{-1}$; $^1$H NMR (400 MHz, CDCl$_3$): δ7.60 (d, J=8.4 Hz, 2H), 7.57-7.55 (m, 2H), 7.47-7.45 (m, 2H), 7.39-7.34 (m, 6H), 7.14 (d, J=8.4 Hz, 2H), 4.41 (d, J =13.2 Hz, 1H), 4.21 (d, J=13.2 Hz, 1H) ppm; $^{13}$C NMR (175 MHz, CDCl$_3$): δ153.1, 147.1, 144.0, 138.8, 136.1, 131.7, 129.0, 128.7, 128.6, 128.4, 126.1, 127.8, 126.5, 126.1, 119.8, 56.2 ppm; HRMS (+ESI) m/z calcd for $[C_{22}H_{16}N_4O_2S]^+$ 401.1072, found 401.1119 ([M+H]$^+$).

4.1.4. General Procedure for the Synthesis of Acetylenic Triazines 25-27:

To a solution of ethynyltrimethylsilane (1.0 equiv) in dry THF (5.0 mL) was added
n-butyllithium (1.6 M solution in hexane, 1.0 equiv) by syringe at 0° C. under argon while stirring. After stirring for one hour at 0° C., a resulting solution of lithioethynyltrimethylsilane was cannulated dropwise onto a solution of cyanuric chloride (1.0 equiv) in dry THF. The resulting viscous red-brown suspension was stirred at 0° C. (2 h) before the corresponding amines (diethylamine, 2-fluoroaniline or 4-fluoroaniline, 2.0 equiv) were added dropwise at 0° C. The reaction temperature was gradually increased to room temperature and allowed to stir for 48 h. After completion of reaction, as monitored by TLC, the reaction mixture was quenched with cold water and extracted into dichloromethane (2×25 mL). The organic layers were combined, dried over anhydrous sodium sulfate and evaporated to give a crude brownish residue which was further purified by using column chromatography to obtain the pure TMS acetylenic triazines 89a-89c. To a prechilled solution of the corresponding trimethylsilyl triazines 89a-89c (1.0 equiv) in dry THF (25 mL) was slowly added tetra-n-butylammonium fluoride (TBAF, 1.0 equiv) under a nitrogen atmosphere. The resulting brown solution was stirred at 5-10° C. (1 h). The progress of the reaction was monitored by TLC (hexane/ethyl acetate, 9:1). After completion of the reaction, cold water (25 mL) was added to the reaction mixture followed by extraction into dichloromethane (2×25 mL). The combined organic layers were dried over anhydrous sodium sulfate, filtered and evaporated to obtain crude residue which was submitted to silica gel column chromatography (hexane/ ethyl acetate, 9:1) to give the pure acetylenic diaminotriazines 25-27 as solid materials.

4.1.4.1. N2,N2,N4,N4-Tetraethyl-6-((trimethylsilyl)ethynyl)-1,3,5-triazine-2,4-diamine (89a): Pale yellow solid; 50% yield; mp=102-103° C.; $R_f$=0.56 (hexane/ethyl acetate, 3:1); FT-IR: 2981, 2964, 2932, 1535, 1493, 1359, 1249, 1079 cm$^{-1}$; $^1$H NMR (400 MHz, CDCl$_3$): δ3.60 (s, 4H), 3.53 (d, J=6.4 Hz, 4H), 1.15 (t, J=7.2 Hz, 12H), 0.26 (s, 9H) ppm; $^{13}$C NMR (125 MHz, CDCl$_3$): δ163.7, 158.3, 110.0, 103.6, 90.6, 40.9, 13.5, 12.8, −0.28 ppm; LRMS (+ESI) for $[C_{16}H_{29}N_5Si]$ found 319.

4.1.4.2. N2,N2,N4,N4Tetraethyl-6-ethynyl-1,3,5-triazine-2,4-diamine (25): Off-white solid; 59% yield; mp=47-49° C.; $R_f$=0.33 (hexane/ethyl acetate, 9:1); FT-IR: 3228, 2977, 2933, 2112, 1539, 1492, 1355, 1084 cm$^{-1}$; $^1$H NMR (400 MHz, CDCl$_3$): δ3.59 (d, J=6.0 Hz, 4H), 3.53 (d, J=6.0 Hz, 4H), 2.87 (s, 1H), 1.15 (t, J=7.2 Hz, 12H) ppm; $^{13}$C NMR (125 MHz, CDCl$_3$): δ163.6, 157.9, 82.7, 72.9, 41.1, 13.5, 12.8 ppm; LRMS (+ESI) for $[C_{13}H_{21}N_5]$ found 247.

4.1.5. General procedure for the synthesis of benzoin esters 58-72: To a clear pre-chilled solution of benzoin, the halogenated benzoins or furoin (1.0 equiv.) in dichloromethane (50 mL) was added DMAP (1.5 equiv.) and stirring was continued (30 min). To the reaction mixture was added dropwise a solution of 2-, 3- or 4-azidobenzoyl chloride (prepared by reacting the corresponding azidocarboxylic acids (1.3 equiv) with thionyl chloride at 85-90° C. for 2 h.), dissolved in dichloromethane (20 mL) under a nitrogen atmosphere. The progress of reaction was monitored by TLC (hexane/ethyl acetate). After completion of the reaction, the reaction mixture was washed with aqueous HCl (5%, 2×50 mL) followed by aqueous NaHCO$_3$ (5%). The organic layer was separated, dried over anhydrous sodium sulfate, filtered and evaporated to obtain the crude residue of corresponding azidobenzoyl esters which were purified by column chromatography on gravity silica gel (hexane/ethyl acetate) to give the pure 2-, 3-, 4-azidobenzoyl esters 58-72.

4.1.5.1. 2-Oxo-1,2-diphenylethyl 2-azidobenzoate (58): Colorless oil; Yield 95%; $R_f$=0.4 (hexane/ethyl acetate, 3:1); FT-IR: 3065, 2118, 2090, 1714, 1686, 1596, 1487, 1235 cm$^{-1}$; $^1$H NMR (400 MHz, CDCl$_3$) δ8.08 (dd, J=1.2 Hz, 7.6 Hz, 1H), 7.98 (dd, J=1.2 Hz, 8.2 Hz, 2H), 7.57-7.51 (m, 4H), 7.44-7.35 (m, 5H), 7.24-7.17 (m. 1H), 7.08 (s, 1H) ppm; $^{13}$C NMR (100 MHz, CDCl$_3$) 193.6, 164.3, 140.6, 134.7, 133.7, 133.5, 133.4, 132.4, 129.4, 129.2, 128.9, 128.7, 128.6, 124.5, 121.4, 119.8, 78.1 ppm; LRMS for $[C_{21}H_{15}N_3O_5]$ found 358 (M+H).

4.1.6. General Procedure for the Synthesis of 4,5-diaryl-2-azidophenyloxazoles 73-87:

The azidobenzoyl esters 58-72 (1.0 equiv) were dissolved in glacial acetic acid (100 mL) at room temperature. To the clear solution was added ammonium acetate (15 equiv) under a nitrogen atmosphere. The resulting reaction mixture was heated at 115° C. (oil bath temperature) and the temperature was maintained for 3 h. After completion of reaction, as indicated by TLC, the reaction mixture was cooled to room temperature. Cold water (150 mL) was added to the reaction mixture which was then slowly neutralized with saturated NaHCO$_3$ solution. The crude product was extracted with dichloromethane (2×50 mL) and the organic extracts were combined, dried over anhydrous sodium sulfate and filtered. Concentration of the dried extracts provided the corresponding crude azido oxazoles which were submitted to silica gel column chromatography (hexane/ethyl acetate) afforded the pure 4,5-diaryl-2-azidophenyloxazoles 73-87.

4.1.6.1. 2-(2-Azidophenyl)-4,5-diphenyloxazole (73): Pale yellow soild; 84% Yield; $R_f$=0.22 (hexane/ethyl acetate, 9:1); FT-IR: 3059, 2121, 2089, 1581, 1501, 1291, 1070 cm$^{-1}$; $^1$H NMR (400 MHz, CDCl$_3$) δ8.32 (d, J=7.6 Hz, 1H), 7.94 (dd, J=8.0 Hz, 18.4 Hz, 4H), 7.70 (t, J=7.6 Hz, 1H), 7.65-7.52 (m, 7H), 7.47 (t, J=8.0 Hz, 1H) ppm; $^{13}$C NMR (100 MHz, CDCl$_3$) δ157.8, 145.9, 138.2, 136.7, 134.9, 132.5, 131.4, 130.7, 129.9, 129.0, 128.9, 128.7, 128.69, 128.64, 128.3, 126.6, 124.9, 119.8, 119.2 ppm; HRMS (ESI) m/z calcd for [C$_{21}$H$_{15}$N$_4$O] 339.1240, found 339.1242.

4.1.7. General Procedure for the Synthesis of the Click Triazole Products 28-57 and 90-124:

To a solution of the group of the azidophenylsulfoxide and sulfone click partners 10-15 and the azidphenyl click partners 73-87 (1.0 equiv) in anhydrous THF (2.0 mL) were added the requisite acetylenic click partners 16-27 (1.1 equiv) followed by addition of solid copper sulfate pentahydrate (0.1 equiv) at room temperature. To the reaction mixture was then added a freshly prepared clear solution of sodium ascorbate (0.5 equiv) in water (1 mL). The resulting reaction mixture was stirred at room temperature (5-16 h). The progress of the reaction was monitored by TLC using the mobile phases hexanes/ethyl acetate and/or chloroform/methanol. After completion of the reaction, the reaction mixture was concentrated and the crude residue was partitioned between dichloromethane (15 mL) and water (10 mL). The organic layer was separated, dried over anhydrous sodium sulfate and concentrated to obtain the crude residue of the click products which were submitted to silica gel column chromatography (hexanes/ethyl acetate, or chloroform/methanol) to give the corresponding pure click product triazoles 28-57 and 90-124.

4.1.7.1. 4,5-Diphenyl-2-(((4-(4-(pyridin-3-yl)-1H-1,2,3-triazol-1-yl)phenyl)sulfinyl) methyl) oxazole (28):

Light yellow solid; yield 48%; mp=193-195° C.; $R_f$=0.26 (methanol/chloroform, 1:9); FT-IR (neat): 3085, 3038, 2986, 2929, 1593, 1507, 1404, 1238, 1049, 687 cm$^{-1}$; $^1$H NMR (400 MHz, CDCl$_3$): δ9.07 (s, 1H), 8.65 (s, 1H), 8.29 (d, J=8.4 Hz, 1H), 8.19 (s, 1H), 7.96 (d, J=8.4 Hz, 2H), 7.82 (d, J=8.0 Hz, 2H), 7.57-7.55 (m, 1H), 7.47-7.42 (m, 3H), 7.37-7.29 (m, 6H), 4.40 (dd, J=14.0 Hz, 68.4 Hz, 2H) ppm; $^{13}$C NMR (175 MHz, CDCl$_3$): δ152.7, 149.8, 147.2, 147.1, 145.8, 143.7, 139.2, 136.2, 133.2, 131.6, 129.0, 128.72, 128.66, 128.51, 128.0, 127.8, 126.5, 126.1, 126.0, 123.9, 121.1, 117.7, 56.1 ppm; HRMS (+ESI) m/z calcd for [C$_{29}$H$_{21}$N$_5$O$_2$S]$^+$ 504.1494, found 504.1516 ([M+H]$^+$).

4.2 Biology 4.2.1. Bacterial Strains and Culture Conditions

*P. gingivalis* ATCC33277 was grown in reduced trypticase soy broth (Difco) supplemented with 0.5 percent yeast extract, 1 μg/mL menadione, and 5 μg/mL hemin. Twenty five milliliters of medium were reduced for 24 h under anaerobic conditions by equilibrating in an atmosphere consisting of 10% CO$_2$, 10% H$_2$, and 80% N$_2$. Following equilibration, *P. gingivalis* was inoculated in the media and grown for 48 h at 37° C. under anaerobic conditions. *S. gordonii* DL-1 (1) was cultured aerobically without shaking in brain heart infusion (BHI) broth supplemented with 1 percent yeast extract for 16 hours at 37° C. For some compounds that inhibited *P. gingivalis* adherence to *S. gordonii*, we determined their affect the planktonic growth of *P. gingivalis* and *S. gordonii*. Broth cultures were grown as described above and compared to cultures grown in the absence of the compound. The concentration of each compound used in the growth inhibition experiments is shown in Tables 2, 3 and 4. Cell density of each culture was determined by measuring the optical density at 600 nm (O.D.$_{600\,nm}$) after 24 h of growth. The percent growth inhibition/stimulation was calculated using the following equation:

[(O.D.$_{600\,nm}$ of the control/O.D.$_{600\,nm}$ of the culture grown in the presence of compound)−1]×100.

4.2.2. Biofilm Model for In Vitro Analysis of *P. Gingivalis* Adherence to *S. Gordonii*

Two species biofilms were formed essentially as previously described [41]. To prepare bacterial cells for biofilm culture, 10 ml of an overnight *S. gordonii* culture was centrifuged at 5600 rpm for 5 min and the cell pellet was suspended in 1 mL sterile PBS. Subsequently, 20 μL of 5 mg/ml hexidium iodide (Molecular Probes) was added to the cell suspension and incubated for 15 min with gentle shaking at room temperature in the dark. The labeled cells were centrifuged as described above, washed with phosphate buffered saline (10 mM Na$_2$HPO$_4$, 18 mM KH$_2$PO$_4$, 1.37 M NaCl, and 2.7 mM KCl, pH 7.2; [PBS]) and the cell pellet was suspended in PBS at a final O.D.$_{600\,nm}$ of 0.8. Similarly, 10 mL of a 48 h culture of *P. gingivalis* was centrifuged at 5600 rpm for 15 min, the cell pellet was suspended in 1 mL PBS and 20 μl of 5(6)-carboxyfluorescein N-hydroxysuccinimide ester (4 mg/ml, Molecular Probes, Inc.) was added. After incubation for 30 min with gentle shaking at room temperature in the dark, the suspension was centrifuged and washed as described above and suspended in PBS at a final O.D.$_{600\,nm}$ of 0.4. For biofilm cultures, 1 mL of labeled *S. gordonii* cells was added to each well of a 12-well microtiter plate (Greiner Bio-one) containing a circular coverslip (Fisher brand) and incubated in an anaerobic chamber with rotary shaking for 24 h at 37° C. Unbound cells were removed by aspiration and 1 ml of labeled *P. gingivalis* cells containing the desired concentration of test compound was added and incubated under anaerobic conditions for 22 h at 37° C. Test compounds were dissolved in dimethylsulfoxide (DMSO) to generate 1000× stock solutions and were routinely tested over a final concentration range of 0-60 μM. 1 μL of the appropriate stock solution was added to each 1 mL aliquot of labeled *P. gingivalis* cells and incubated for 30 min at room temperature prior to adding the suspension to the microtiter plate wells. For control biofilms, 1 μL of DMSO was added to 1 mL of labeled *P. gingivalis* and incubated as described above.

4.2.3. Visualization of Two Species Biofilms.

To visualize *P. gingivalis/S. gordonii* biofilms, unbound *P. gingivalis* cells were removed by aspiration and coverslips were washed once with PBS. Biofilms were fixed by incubating the coverslips with 1 mL of 4% paraformaldehyde for 5 min followed by two washes with PBS. The coverslips were then removed, placed face down on a glass microscope slide containing a drop of antifade reagent (Life Technology) and sealed with nail polish. Visualization of biofilms was carried out by laser scanning confocal microscopy using a Leica SP8 confocal microscope (Leica Microsystems Inc., Buffalo Grove, IL) using a 488 nm laser to detect labeled *P. gingivalis* and a 552 nm laser to detect *S. gordonii*. Z-plane scans of 25 μm in depth were collected at three randomly chosen frames on each coverslip using a z-step thickness of 0.7 μm. Background noise was minimized using software provided with the Leica SP8 and three dimensional reconstruction of the Z-plane scans and quantification of total green and red fluorescence was conducted using Volocity 6.3 Image analysis software (Perkin Elmer, Akron, Ohio). Data was expressed as the ratio of total green (*P. gingivalis*) to red Example 1 References

[1] S. S. Socransky, A. D. Haffajee, M. A. Cugini, C. Smith, R. L. Kent, Jr., Microbial Complexes in Subgingival plaque, J. Clin. Periodontol. 25 (1998)134-144.

[2] G. Hajishengallis, S. Liang, M. A. Payne, A. Hashim, R. Jotwani, M. A. Eskan, M. L. McIntosh, A. Alsam, K. L. Kirkwood, J. D. Lambris, R. P. Darveau, M. A. Curtis, Low abundance biofilm species orchestrates inflammatory periodontal disease through the commensal microbiota and complement, Cell Host Microbe 10 (2011) 497-506.

[3] R. J. Lamont, G. Hajishengallis, Polymicrobial synergy and dysbiosis in inflammatory disease, Trends Mol. Med. 21 (2015) 172-183. PMID 25498392

[4] G. Hajishengallis, R. J. Lamont, Dancing with the stars: How choreographed bacterial interactions dictate nososymbiocity and give rise to keystone pathogens, accessory pathogens and pathobionts, Trends Microbiol. 24 (2016) 477-489. PMID 26968354.

[5] G. Hajishengallis, R. P. Darveau, M. A. Curtiss, The keystone pathogen hypothesis,
Nature Rev. Microbiol. 10 (2012) 717-725.

[6] C. J. Wright, L. H. Burns, A. A. Jack, C. R. Back, L. C. Dutton, A. H. Nobbs, R. J. Lamont, H. F. Jenkinson, Microbial Interactions in Building of Communities, Mol. Oral Microbiol., 28 (2013) 83-101.

[7] R. J. Lamont, A. El-Sabaeny, Y. Park, G. S. Cook, J. W. Costerton, D. R. Demuth, Role of *Streptococcus gordonii* SspB protein in the development of *Porphyromonas gingivalis* biofilms on streptococcal substrates, Microbiology 148 (2002)1627-1636.

[8] Y. Park, M. R. Simionato, K. Sekiya, Y. Murakami, D. James, W. Chen, M. Hackett, D. R Demuth, R. J. Lamont, Short Fimbriae of *Porphyromonas gingivalis* and their Role in Coadhesion with *Streptococcus gordonii*, Infect. Immun. 73 (2005) 3983-3989.

[9] C. A. Daep, D. M. James, R. J. Lamont, D. R. Demuth, Structural Characterization of Peptide-Mediated Inhibition of *Porphyromonas gingivalis* Biofilm Formation, Infect. Immun. 74 (2006) 5756-5762.

[10] C. A. Daep, R. J. Lamont, D. R. Demuth, Interaction of *Porphyromonas gingivalis* with Oral streptococci Requires a Motif that Resembles the Eukaryotic Nuclear Receptor Box Domain, Infect. Immun. 76 (2008) 3272-3280.

[11] C. A. Daep, E. A. Novak, R. J. Lamont, D. R. Demuth, Structural dissection and in vivo Effectiveness of a peptide inhibitor of *Porphyromonas gingivalis* adherence to *Streptococcus gordonii*, Infect. Immun. 79 (2011) 67-74.

[12] P. C. Patil, J. Tan, D.R Demuth, F. A. Luzzio, 1,2,3-Triazole-Based inhibitors of *Porphyromonas gingivalis* adherence to oral streptococci and biofilm formation, Bioorg. Med. Chem. 24 (2016) 5410-5417.

[13] J. Tan, P. C. Patil, F. A. Luzzio, D. R. Demuth, In vitro and In vivo activity of peptidomimetic compounds that target the periodontal pathogen *Porphyromonas gingivalis* Antimicrob. Agent. Chemother. 2018. doi:10.1128/AAC.00400-18.

[14] V. P. Mocharla, B. Colasson, L. V. Lee, S. Roper, K. B. Sharpless, C. H. Wong, H. C. Kolb, In situ click Chemistry: Enzyme-generated inhibitors of Carbonic anhydrase II, Angew. Chem. Int. Ed. 44 (2005) 116-120.

[15] S. Borman, In Situ Click Chemistry, Chem. Eng. News 80 (2002) 29-29.

[16] M. Gehringer, S. A. Laufer, Click Chemistry: Novel Applications in Cell Biology and Drug Discovery, Angew. Chem. Int. Ed. 56 (2017) 2-4.

[17] M. S. Singh, S. Chowdury, S. Koley, Advances in Azide-Alkyne Cycloaddition-Click Chemistry Over the Recent Decade, Tetrahedron 72 (2016) 5257-5383.

[18] J. Totobenazara, A. J. Burke, New Click-Chemistry Methods for 1,2,3-Triazoles Synthesis: Recent Advances and Applications, Tetrahedron Lett. 56 (2015) 2853-2859.

[19] K. C. Majumdar, K. Ray, Synthesis of 1,2,3-Triazole-Fused Heterocycles via Intramolecular Azide-Alkyne Cycloaddition Reactions, Synthesis 23 (2011) 3767-3783.

[20] C. D. Hein, X.-M. Liu, D. Wang, Click Chemistry, A Powerful Tool for Pharmaceutical Sciences Pharmaceutical Res. 25 (2008) 2216-2230.

[21] M. Meldal, C. W Tornøe, Cu-Catalyzed Azide-Alkyne Cycloaddition, Chem. Rev. 108 (2008) 2952-3015.

[22] J. E. Moses, A. D. Moorhouse, The Growing Applications of Click Chemistry, Chem. Soc. Rev. 37 (2007)1249-1262.

[23] C. M. Loner, F. A. Luzzio, D. R. Demuth, Preparation of Azidoaryl- and Azidoalkyloxazoles for Click Chemistry, Tetrahedron Lett. 53 (2012) 5641-5644.

[24] P. C. Patil, F. A. Luzzio, D. R. Demuth, Oxazoles for Click Chemistrry II: Synthesis of Extended Heterocyclic Scaffolds, Tetrahedron Lett. 56 (2015) 3039-3041.

[25] P. C. Patil, F. A. Luzzio, Synthesis of Extended Oxazoles II: Reaction manifold of 2-(Halomethyl)-4,5-Diaryloxazoles, Tetrahedron Lett. 57 (2016) 757-759.

[26] P. C. Patil, F. A. Luzzio, Synthesis of Extended Oxazoles III: Reactions of 2-(Phenylsulfonyl)methyl-4,5-Diaryloxazoles, J. Org. Chem. 81 (2017) 10521-10526.

[27] C. Bissantz, B. Kuhn, M. Stahl, A Medicinal Chemists Guide to Molecular Interactions J. Med. Chem. 53 (2010) 5061-5084.

[28] A. Luzar, D. Chandler, Structure and Hydrogen Bond Dynamics of Water-Dimethylsulfoxide mixtures by Computer Simulations, J. Chem. Phys. 98 (1993) 8160-8173.

[29] L. -G. Milroy, L. Nieto, L. Brunsveld, Targeting Alpha-Helix Based Protein Interactions; Nuclear Receptors as a Case Study, Amino Acids, Pept. Proteins 37 (2012) 238-272.

[30] J. R. Gunther, T. W. Moore, M. L. Collins, J. A. Katzenellenbogen, Amphipathic Benzenes are Designed Inhibitors of the Estrogen Receptor α/Steroid Receptor Coactivator Interaction ACS Chem. Biol. 5(2008) 282-286.

[31] A. L. Rodriguez, A. Tamrazi, M. L. Collins, J. A. Katzenellenbogen, Design, Synthesis, and In Vitro Biological Evaluation of Small Molecule Inhibitors of Estrogen Receptor α Coactivator Binding, J. Med. Chem. 47 (2004) 600-611.

[32] N. A. Meanwell, Fluorine and Fluorinated Motifs in the Design and Application of Bioisosteres for Drug Design, J. Med. Chem. 2018, DOI: 10:1021/acs.jmedchem.7b01788.

[33] E. P. Gillis, K. J. Eastman, M. C. Hill, D. J. Connelly, N. A. Meanwell, N. A., Applications of Fluorine in Medicinal Chemistry, J. Med. Chem. 58 (2015) 8315-8359.

[34] P. Shah, A. D. Westwell, The Role of Fluorine in Medicinal Chemistry, J. Enzyme Inhib. Med. Chem. 22 (2007) 527-540.

[35] H.-J. Böhm, D. Banner, S. Bensels, M. Kansy, B. Kuhn, K. Müller, U. Obst-Sander, M. Stahl, Fluorine in Medicinal Chemistry, ChemBioChem 5 (2004) 637-643.

[36] J. B. Sperry, D. L. Wright, Furans, Thiophenes and Related Heterocycles in Drug Discovery, Curr. Opin. Drug. Disc. Devel. 8 (2005) 723-740.

[37] V. D. Bock, D. Speijer, H. Hiemstra, J. H. van Maarseveen, 1,2,3-Triazoles as peptide bond isosteres: synthesis and biological evaluation of cyclotetrapeptide mimics, Org. Biomol. Chem. 5 (2007) 971-975.

[38] D. S. Pedersen, A. Abell, 1,2,3-Triazoles in Peptidomimetic Chemistry, Eur. J. Org. Chem. (2011) 2399-2411.

[39] M. Falorni, G. Giacomelli, A. Porcheddu, G. Dettori, New Oxazole-Based Conformationally Restricted Peptidomimetics: Design and Synthesis of Pseudopeptides, Eur. J. Org. Chem. (2000) 3217-3222.

[40] J. Becerril, J. M. Rodriguez, P. N. Wyrembak, A. D. Hamilton, Inhibition of Protein-Protein Interactions by Peptide Mimics, in: E. Giralt, M. W. Peczuh, X. Salvatella (Eds.), Protein Surface Recognition: Approaches for Drug Discovery, John Wiley and Sons, Ltd., New York, 2011, pp. 105-131.

[41] K. Maeda, G. T Tribble, C. M. Tucker, C. Anaya, S. Shizukuishi, J. P. Lewis, D. R. Demuth, R. J. Lamont, *Porphyromonas gingivalis* tyrosine phosphatase is a multifunctional regulator of virulence attributes, Mol. Microbiol. 69 (2008) 1153-1166.

Example 2

Figure 3:
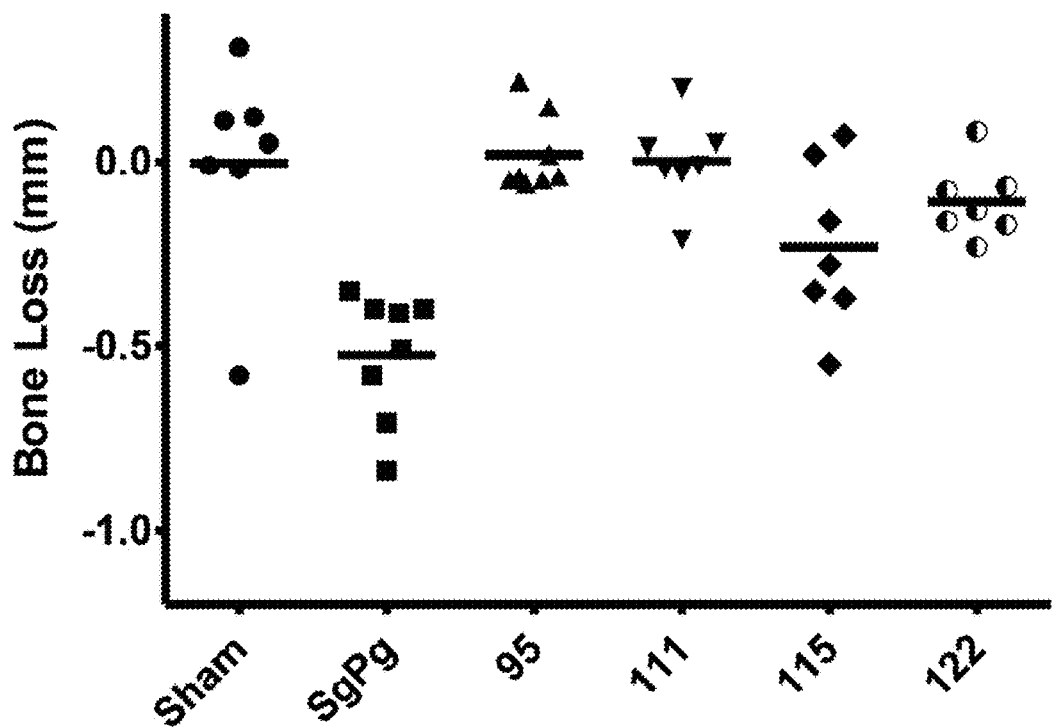
FIG. 3. In vivo reduction of *P. gingivalis*-mediated bone loss (virulence) in mice.
Figure 4A:
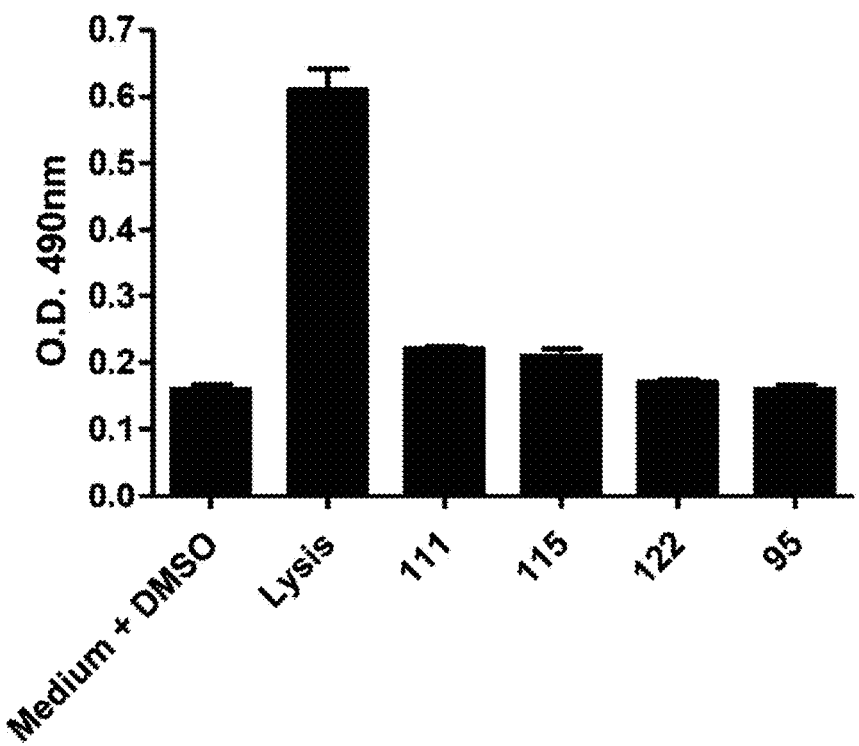
FIG. 4A. LDH release (cell lysis) induced in gingival keratinocytes by compounds 95, 111, 115 and 122.
Figure 4B:
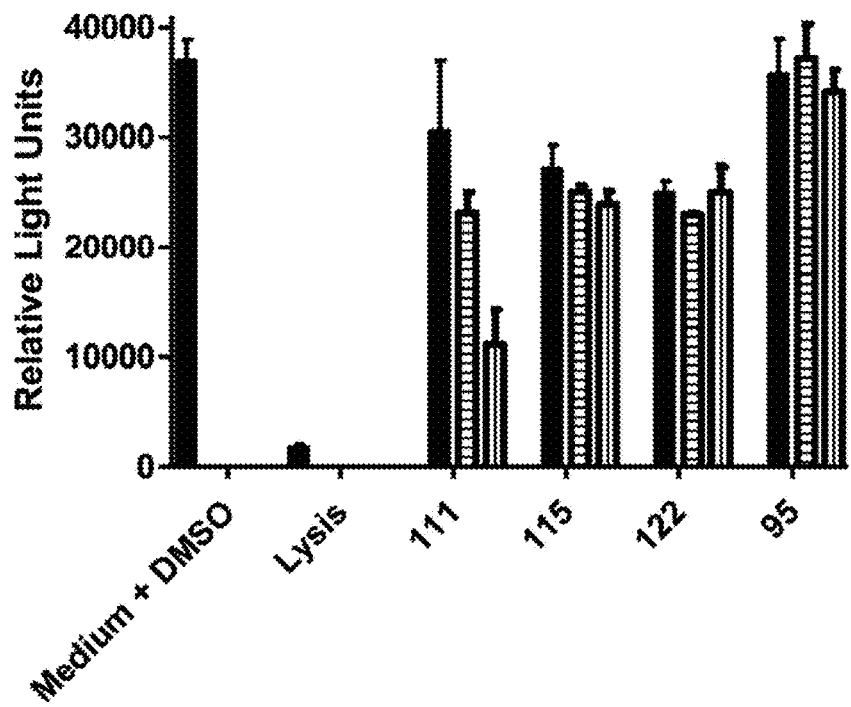
FIG. 4B. Viability (ATP content) of in gingival keratinocytes treated with compounds 95, 111, 115 and 122.
Figure 5:
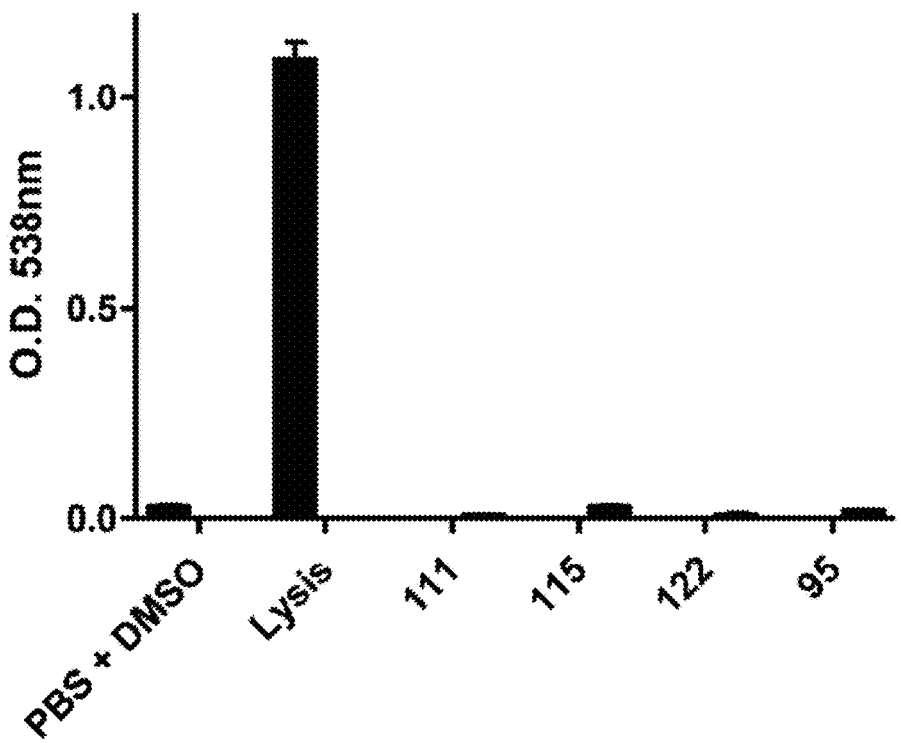
FIG. 5. Hemolytic activity of compounds 95, 111, 115 and 122.

Compounds were capable of disrupting a pre-existing 3-species biofilm in vitro (Table 5), significantly reduced *P. gingivalis*-mediated alveolar bone loss in treated mice versus control (FIG. 3), and exhibited minimal toxicity towards gingival keratinocytes as measured by LDH release (cell lysis, FIG. 4A), cell viability (total ATP content, FIG. 4B) or induction of apoptosis (Table 6). None of the compounds exhibited hemolytic activity against human RBCs (FIG. 5).

TABLE 5

| Time treated | Cmpd 111, 20 μM | Cmpd 115, 20 μM | Cmpd 122, 20 μM | Cmpd 95, 20 μM |
|---|---|---|---|---|
| 3 h | 56.63 | 76.06 | 68.82 | 81 |
| 2 h | 7.33 | 45.62 | 25.71 | 52.84 |
| 1 h | 0.62 | 15.26 | 0 | 16.47 |

TABLE 6

| Compound (concentration) | late apoptosis | early apoptosis | live cells |
|---|---|---|---|
| 111 (5 μM) | 2.36 | 4.96 | 89.25 |
| 111 (20 μM) | 3.39 | 5.06 | 87.95 |
| 111 (60 μM) | 4.38 | 5.60 | 84.40 |
| 115 (5 μM) | 4.21 | 3.89 | 87.85 |
| 115 (10 μM) | 2.47 | 4.07 | 91.25 |
| 115 (20 μM) | 2.80 | 4.06 | 91.20 |
| 122 (5 μM) | 3.95 | 4.50 | 88.30 |
| 122 (20 μM) | 2.92 | 5.93 | 88.80 |
| 122 (60 μM) | 4.59 | 7.54 | 83.65 |
| 95 (5 μM) | 4.27 | 5.02 | 88.50 |
| 95 (20 μM) | 4.26 | 4.89 | 88.35 |
| 95 (40 μM) | 2.83 | 3.80 | 91.75 |
| Media | 6.17 | 5.91 | 85.70 |
| DMSO | 3.13 | 4.60 | 90.30 |
| $H_2O_2$ 4 mM 1 h | 41.50 | 35.60 | 11.30 |

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula I:

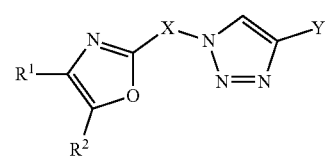

wherein:

X is —$(CH_2)S(=O)_n$phenyl—; or

X is phenyl and (a) at least one of $R^1$ or $R^2$ is an optionally substituted 5-6 membered heteroaryl; or (b) Y is heteroaryl, $(C_3-C_7)$carbocycle, or aryl wherein the heteroaryl, $(C_3-C_7)$carbocycle, or aryl is substituted with at least one —$NR_jR_k$ wherein at least one of Rj or Rk is optionally substituted phenyl and wherein the heteroaryl, $(C_3-C_7)$carbocycle, or aryl is further optionally substituted with one or more $Z^1$ groups;

n is 1 or 2;

Y is heteroaryl, $(C_3-C_7)$carbocycle, or aryl wherein any heteroaryl, $(C_3-C_7)$carbocycle, or aryl of Y is optionally substituted with one or more $Z^1$ groups;

$R^1$ is $(C_1-C_8)$alkyl, $(C_2-C_8)$alkenyl, $(C_2-C_8)$alkynyl, aryl, or 5-6 membered heteroaryl wherein the aryl or 5-6 membered heteroaryl is optionally substituted with one or more groups selected from the group consisting of $(C_1-C_8)$alkyl, $(C_2-C_8)$alkenyl, $(C_2-C_8)$alkynyl, $(C_3-C_7)$carbocycle, halo $(C_1-C_3)$alkyl, —CN, $NO_2$, halogen, —$OR_a$, —$SR_a$, —$S(O)_2NR_bR_c$, —$NR_bR_c$, —$NR_aCOR_a$, —$C(O)R_a$, —$C(O)OR_a$, and —$C(O)NR_bR_c$;

$R^2$ is $(C_1-C_8)$alkyl, $(C_2-C_8)$alkenyl, $(C_2-C_8)$alkynyl, aryl, or 5-6 membered heteroaryl wherein the aryl or 5-6 membered heteroaryl is optionally substituted with one or more groups selected from the group consisting of $(C_1-C_8)$alkyl, $(C_2-C_8)$alkenyl, $(C_2-C_8)$alkynyl, $(C_3-C_7)$carbocycle, halo$(C_1-C_3)$alkyl, —CN, $NO_2$, halogen, —$OR_e$, —$SR_e$, —$S(O)_2NR_fR_g$, —$NR_fR_g$, —$NR_eCOR_h$, —$C(O)R_e$, —$C(O)OR_e$, and —$C(O)NR_fR_g$;

each $R_a$ is independently selected from the group consisting of H, $(C_1-C_6)$alkyl, $(C_2-C_8)$alkenyl, $(C_2-C_8)$alkynyl, $(C_3-C_7)$carbocycle, and aryl;

$R_b$ and $R_c$ are each independently selected from the group consisting of H, $(C_1-C_8)$alkyl, $(C_2-C_8)$alkenyl, $(C_2-C_8)$alkynyl, $(C_3-C_7)$carbocycle and aryl, or $R_b$ and $R_c$ together with the nitrogen to which they are attached form a 5, 6 or 7-membered heterocycle;

$R_d$ is independently selected from the group consisting of $(C_1-C_8)$alkyl, $(C_2-C_8)$alkenyl, $(C_2-C_8)$alkynyl, $(C_3-C_7)$carbocycle, and aryl;

each $R_e$ is independently selected from the group consisting of H, $(C_1-C_8)$alkyl, $(C_2-C_8)$alkenyl, $(C_2-C_8)$alkynyl, $(C_3-C_7)$carbocycle, and aryl;

$R_f$ and $R_g$ are each independently selected from the group consisting of H, $(C_1-C_8)$alkyl, $(C_2-C_8)$alkenyl, $(C_2-C_8)$alkynyl, $(C_3-C_7)$carbocycle and aryl, or $R_f$ and $R_g$ together with the nitrogen to which they are attached form a 5, 6 or 7-membered heterocycle;

$R_h$ is selected from the group consisting of $(C_1-C_8)$alkyl, $(C_2-C_8)$alkenyl, $(C_2-C_8)$alkynyl, $(C_3-C_7)$carbocycle and aryl;

each $Z^1$ is independently selected from the group consisting of halogen, $(C_1-C_8)$alkyl, $(C_2-C_8)$alkenyl, $(C_2-C_8)$alkynyl, $(C_1-C_6)$haloalkyl, —$OR_i$, —$NR_jR_k$ and —$NR_iOR_m$;

$R_i$ is H, $(C_1-C_6)$alkyl, $(C_1-C_6)$haloalkyl or phenyl wherein phenyl is optionally substituted with one or more halogen or $(C_1-C_6)$alkyl;

$R_j$ and $R_k$ are each independently selected from H, $(C_1-C_8)$alkyl or phenyl wherein phenyl is optionally substituted with one or more halogen or $(C_1-C_6)$alkyl;

$R_m$ is $(C_1-C_6)$alkyl or a salt thereof.

2. The compound of claim 1, wherein $R^1$ is aryl, or 5-6 membered heteroaryl wherein the aryl or 5-6 membered heteroaryl is optionally substituted with one or more groups independently selected from the group consisting of $(C_1-C_8)$alkyl, $(C_2-C_8)$alkenyl, $(C_2-C_8)$alkynyl, $(C_3-C_7)$carbocycle, halo $(C_1-C_3)$alkyl, —CN, $NO_2$, halogen, —$OR_a$, —$SR_a$, —$S(O)_2NR_bR_c$, —$NR_bR_c$, —$NR_aCOR_d$, —$C(O)R_a$, —$C(O)OR_a$, and —$C(O)NR_bR_c$.

3. The compound of claim 1, wherein $R^1$ is phenyl or 5-6 membered heteroaryl wherein the phenyl or 5-6 membered heteroaryl is optionally substituted with one or more groups independently selected from the group consisting of $(C_1-C_8)$alkyl, halo$(C_1-C_3)$alkyl, and halogen.

4. The compound of claim 1, wherein $R^1$ is phenyl wherein the phenyl is optionally substituted with one or more groups independently selected from the group consisting of halogen.

5. The compound of claim 1, wherein $R^2$ is aryl, or 5-6 membered heteroaryl wherein the aryl or 5-6 membered heteroaryl is optionally substituted with one or more groups independently selected from the group consisting of $(C_1-C_8)$alkyl, $(C_2-C_8)$alkenyl, $(C_2-C_8)$alkynyl, $(C_3-C_7)$carbocycle, halo$(C_1-C_3)$alkyl, —CN, $NO_2$, halogen, —$OR_e$, —$SR_e$, —$S(O)_2NR_fR_g$, —$NR_fR_g$, —$NR_eCOR_h$, —$C(O)R_e$, —$C(O)OR_e$, and —$C(O)NR_fR_g$.

6. The compound of claim 1, wherein Y is heteroaryl or aryl wherein any heteroaryl, or aryl of Y is optionally substituted with one or more $Z^1$ groups.

7. The compound of claim 1, wherein each $Z^1$ is independently selected from the group consisting of halogen, $(C_1-C_8)$alkyl, $(C_1-C_6)$haloalkyl, and —$OR_i$.

8. The compound of claim 1, wherein Y is pyridinyl, fluorophenyl, methoxyphenyl, trifluoromethylphenyl, methoxynaphthyl, pentylphenyl, phenoxyphenyl, or di-(trifluoromethy)phenyl.

9. The compound of claim 1 that is selected from the group consisting of

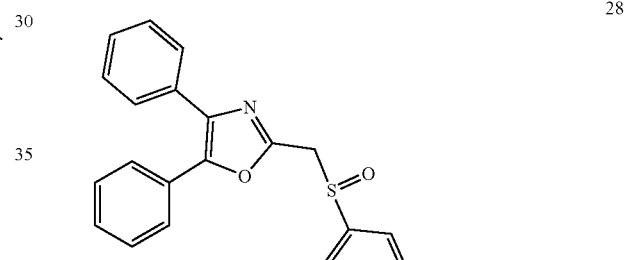

28

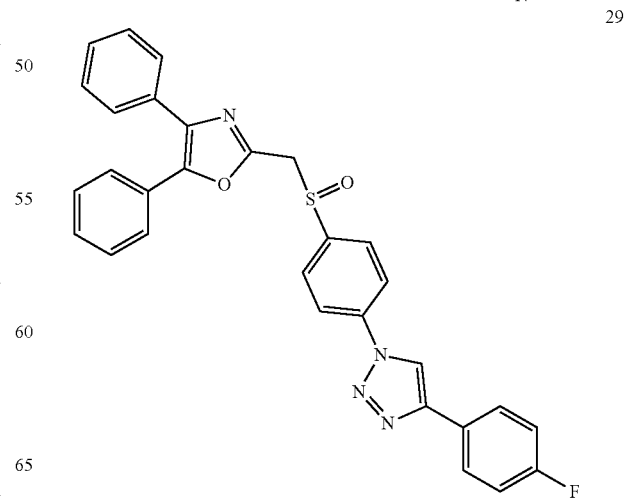

29

30
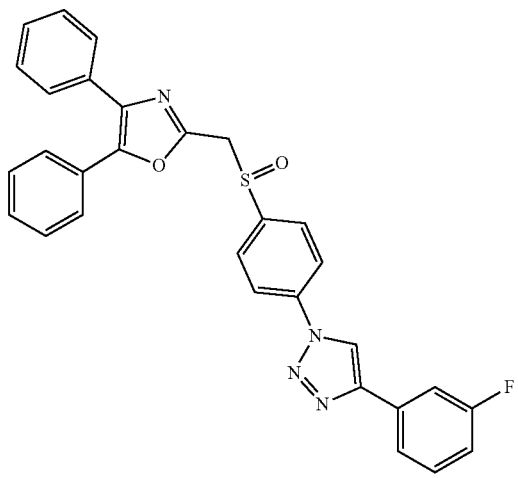
31
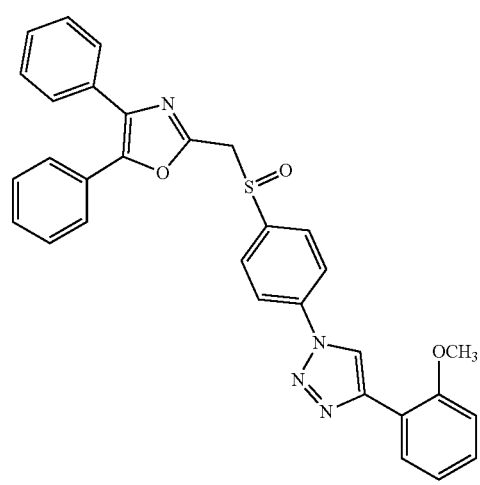
32
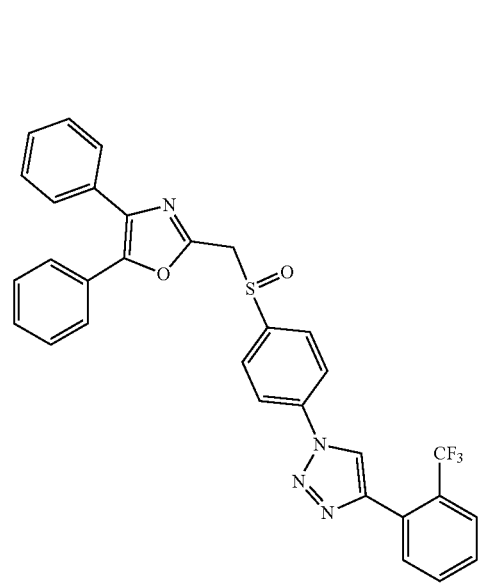
33
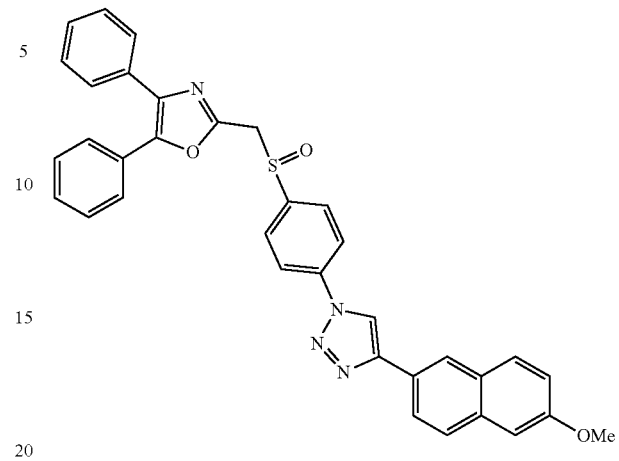
34
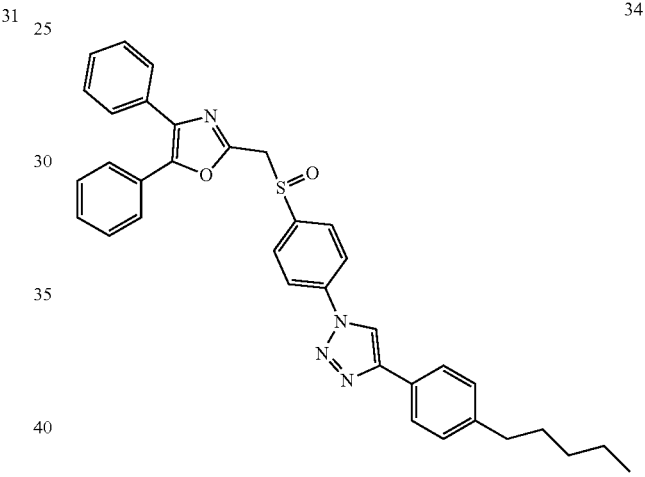
35
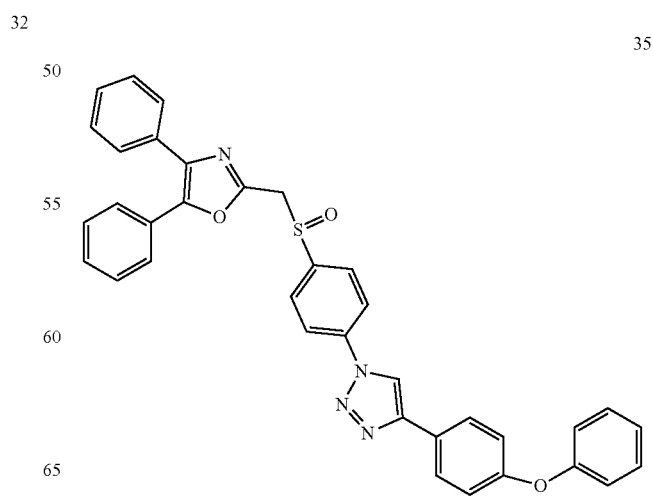

36
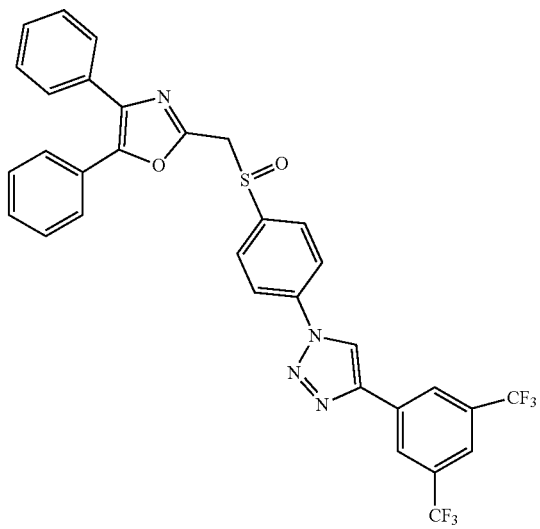
37
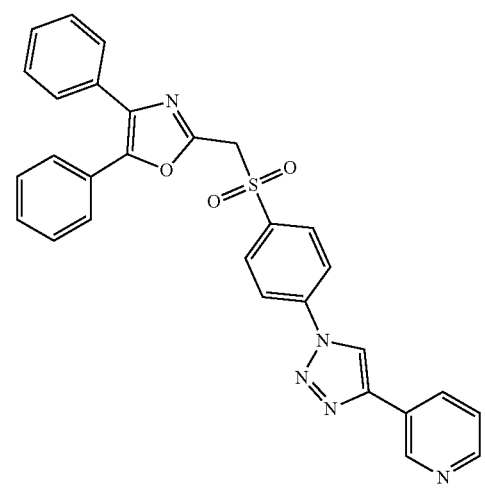
38
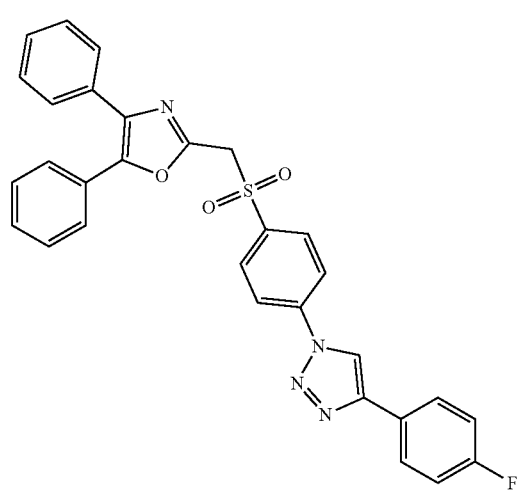
39
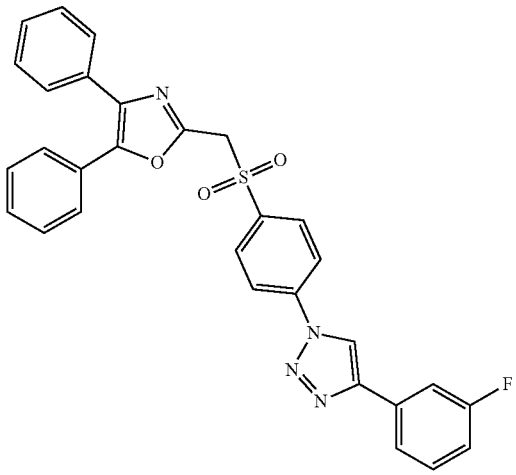
40
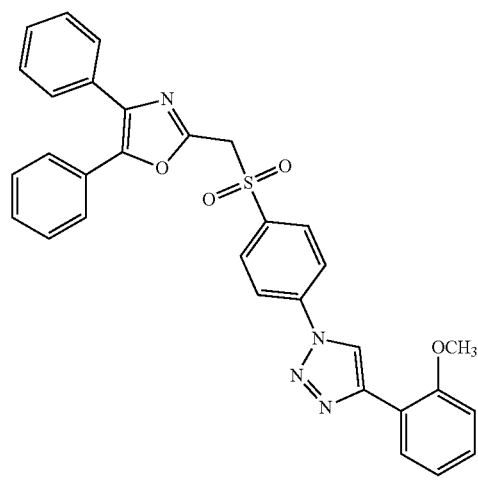
41
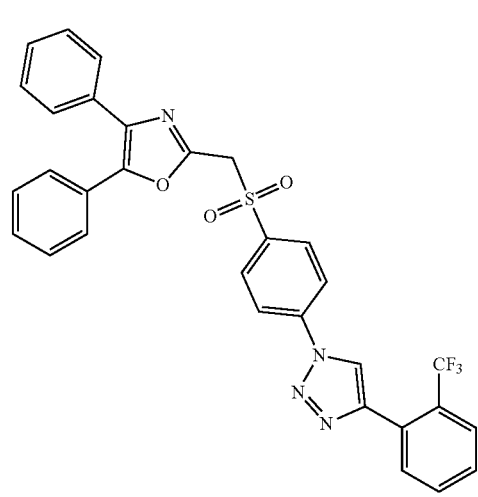

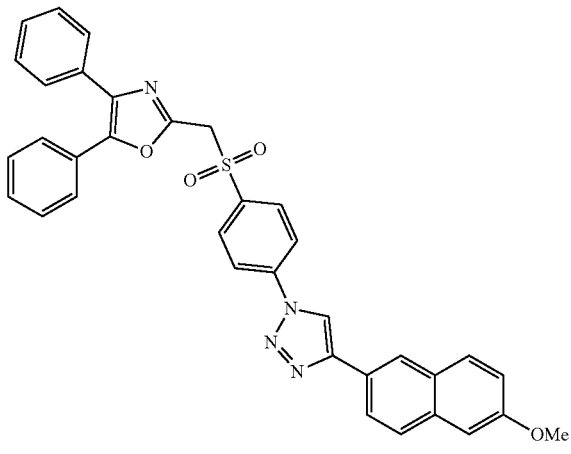
42
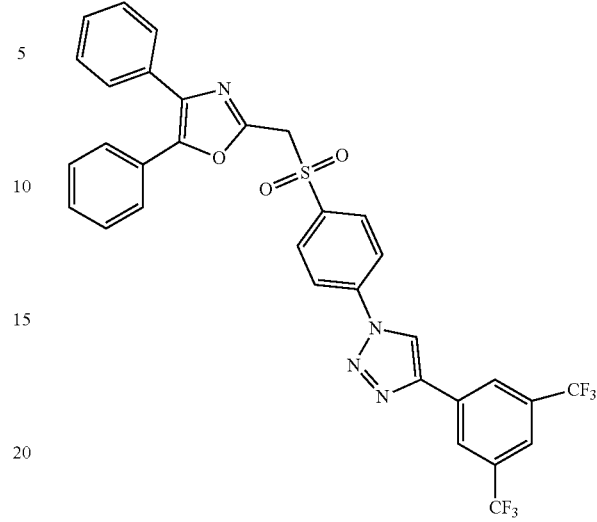
45
43
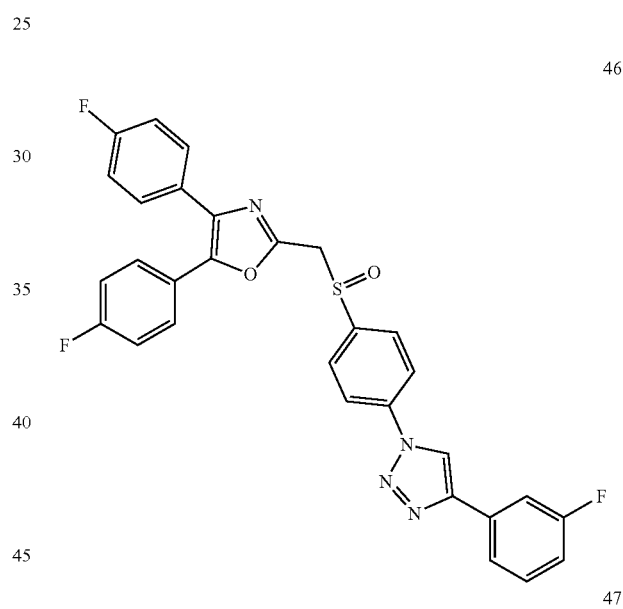
46
44
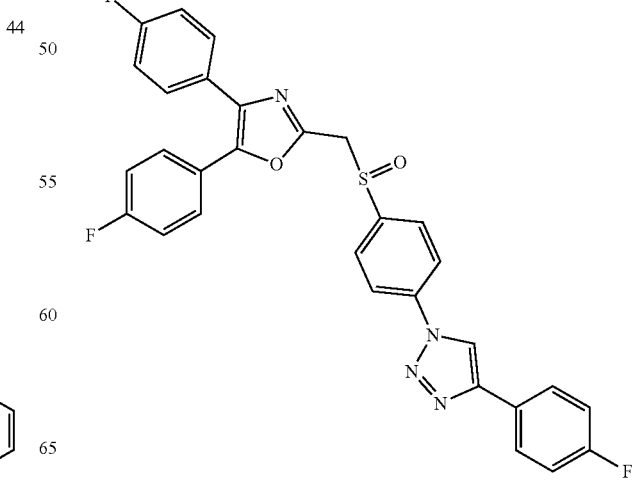
47

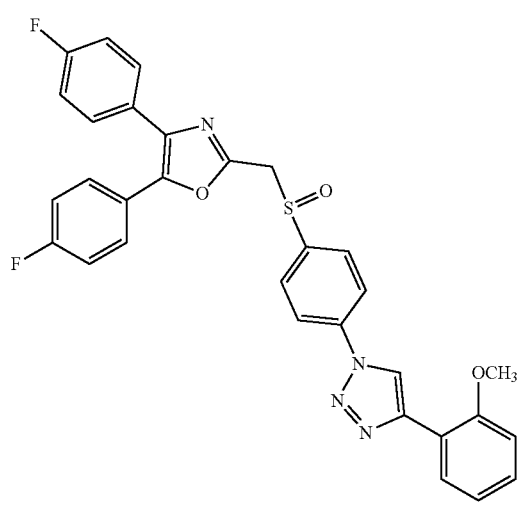
48
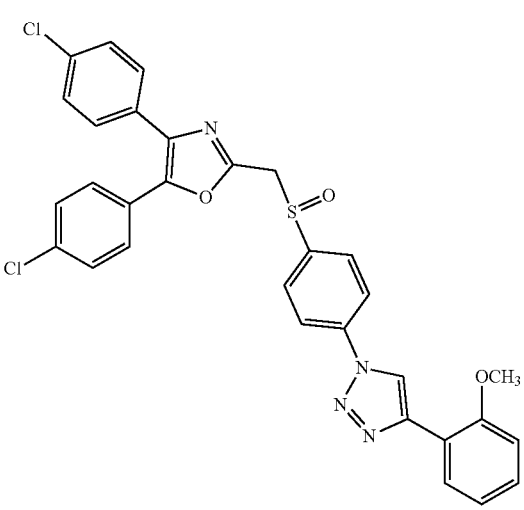
51
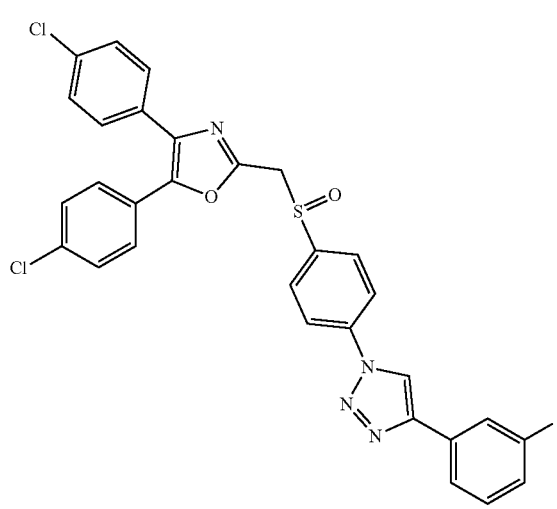
49
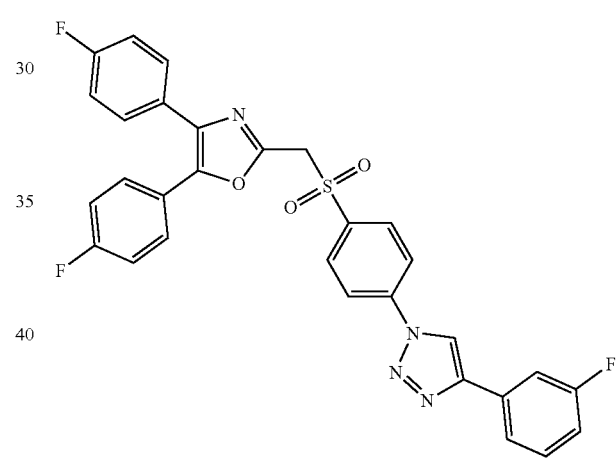
52
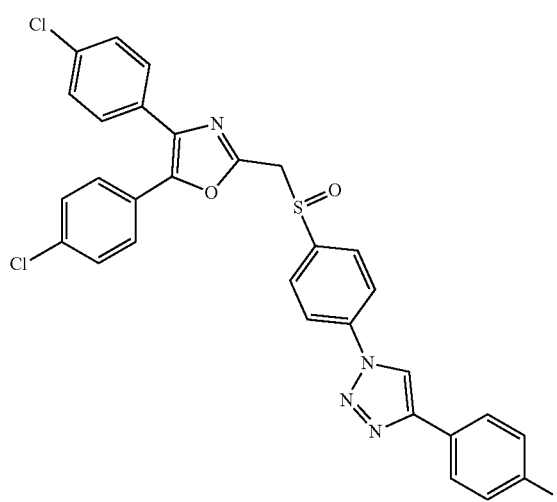
50
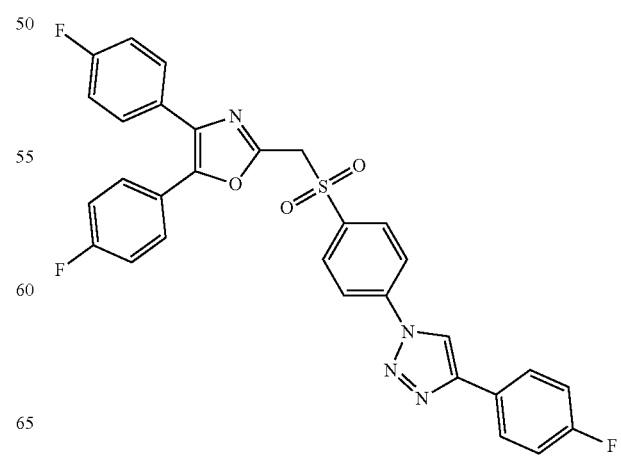
53

54
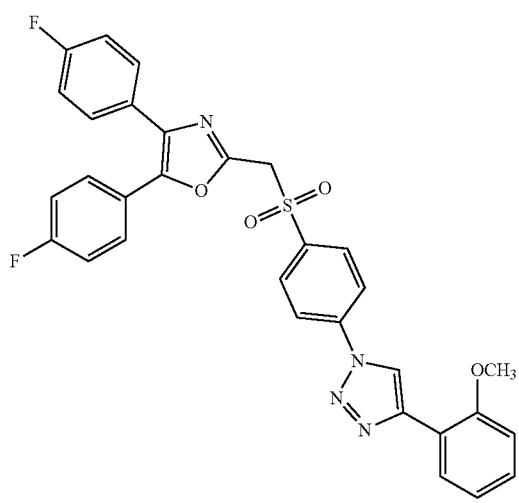
55
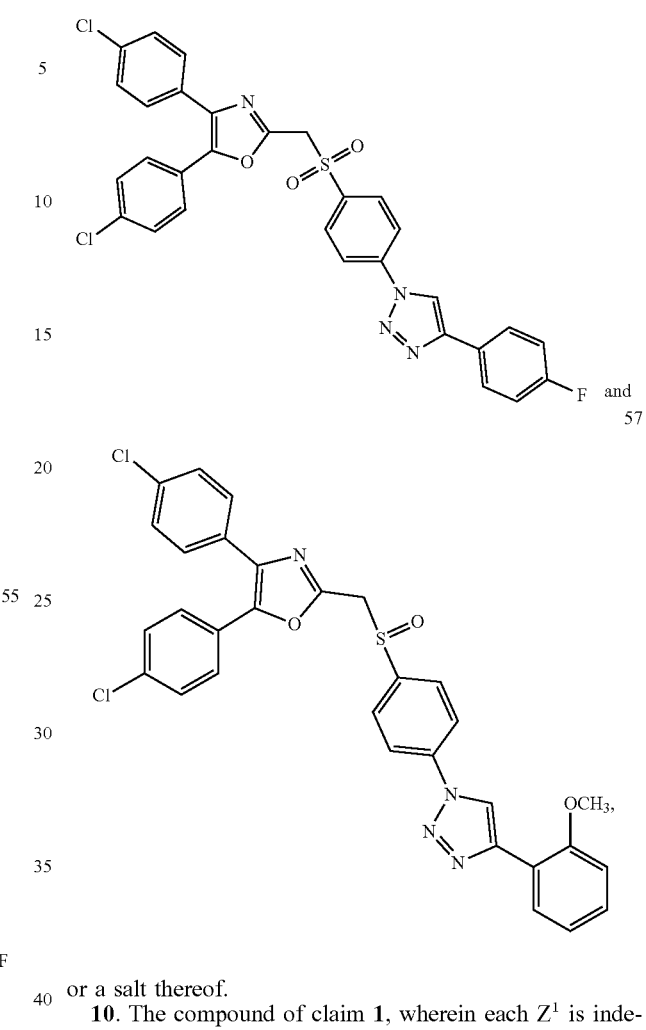
56
or a salt thereof.
10. The compound of claim 1, wherein each $Z^1$ is independently selected from —$NR_jR_k$.
11. The compound of claim 1 that is selected from the group consisting of
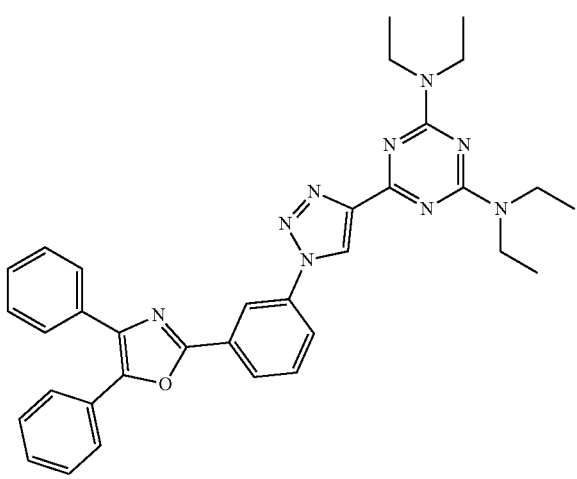

91
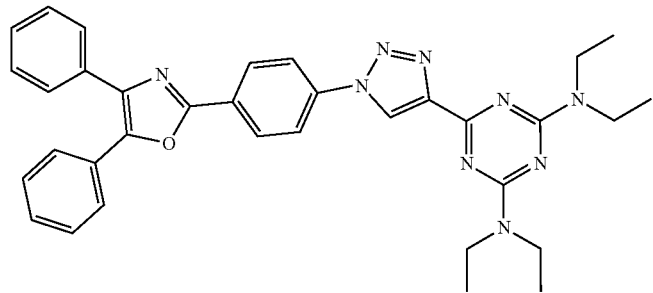
92
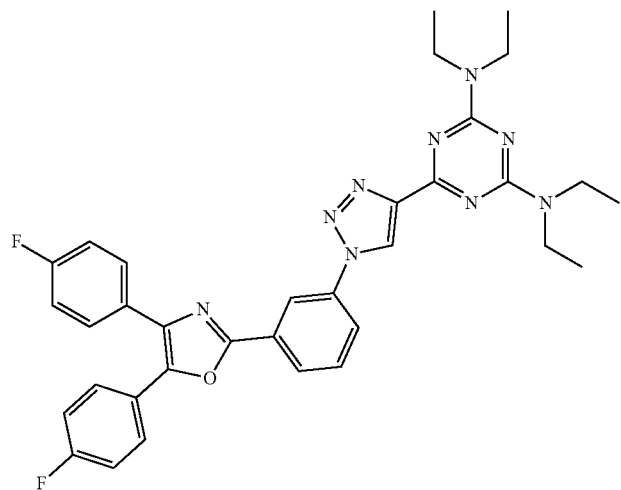
93
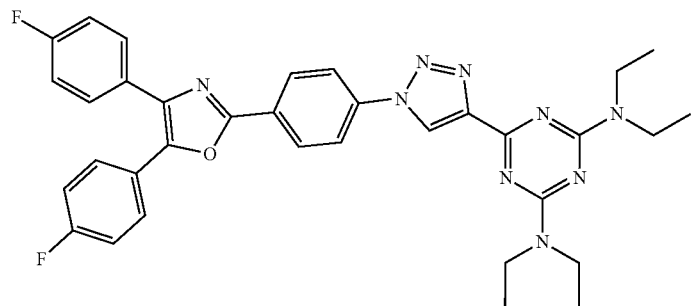
94
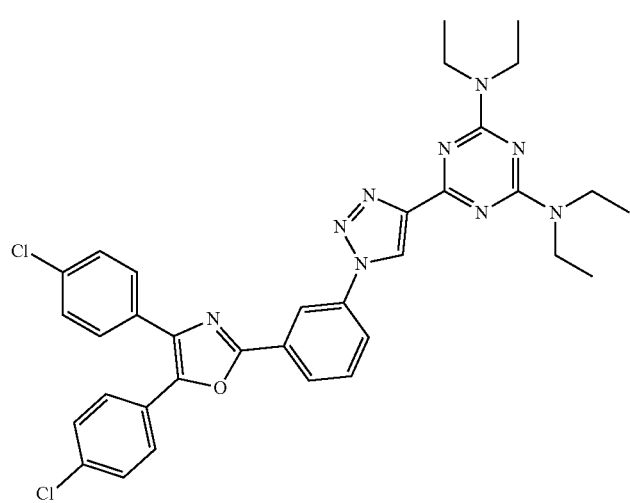

95
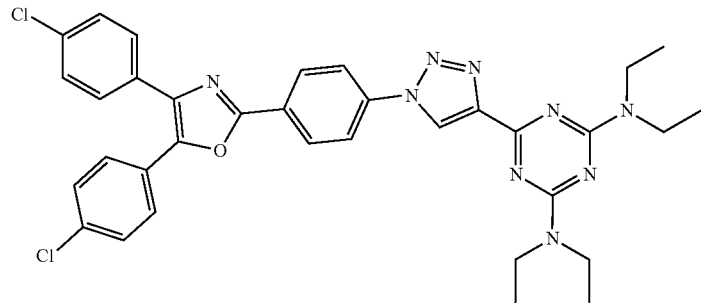
96
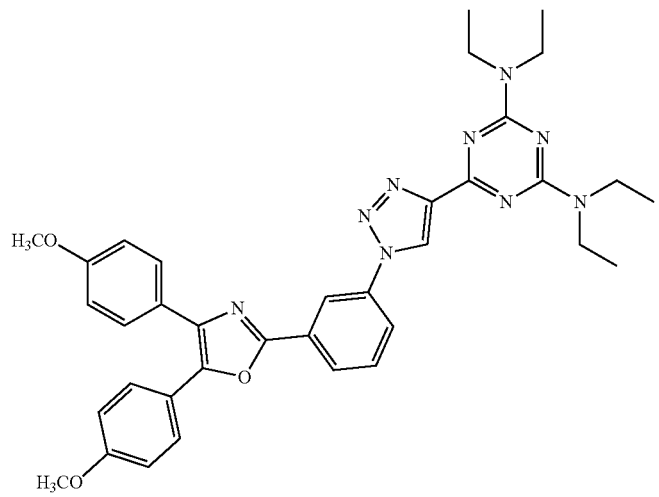
97
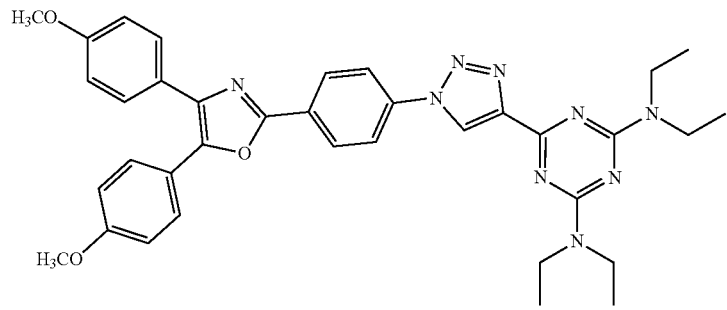
98
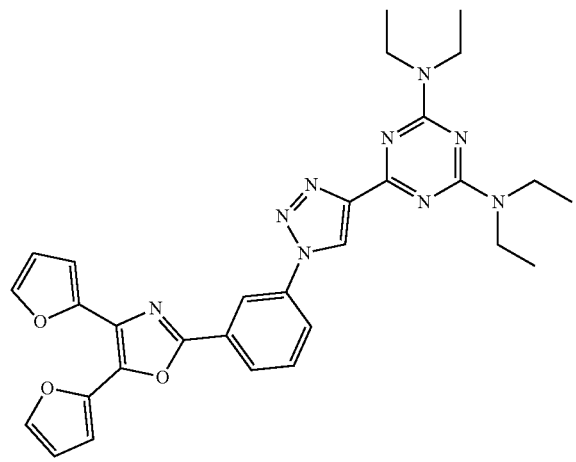

99
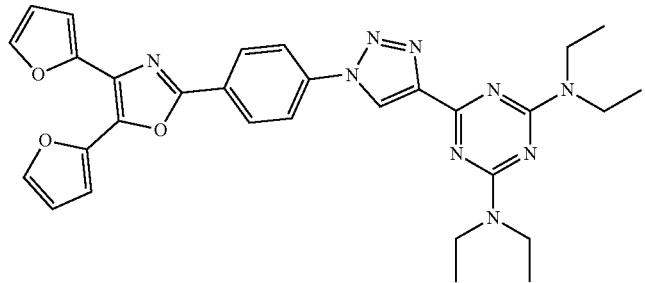
100
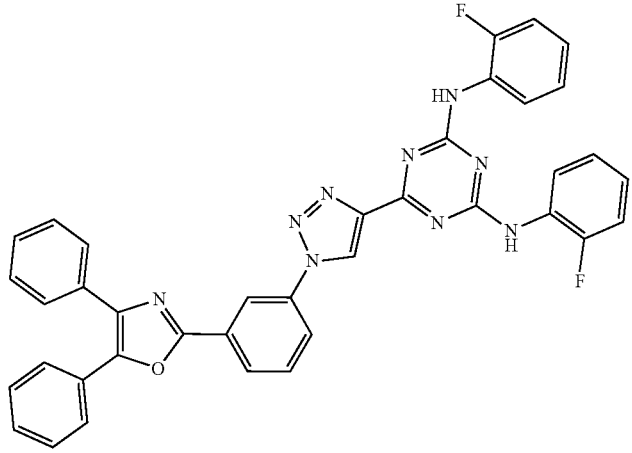
101
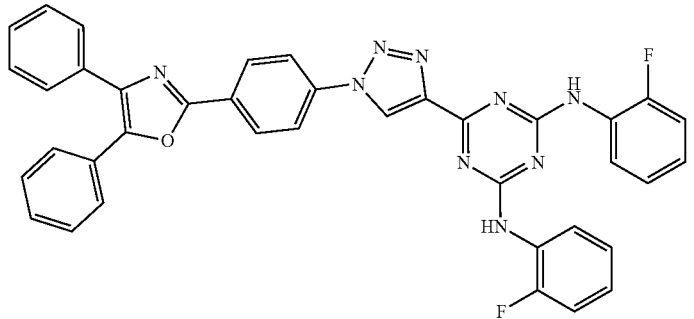
102
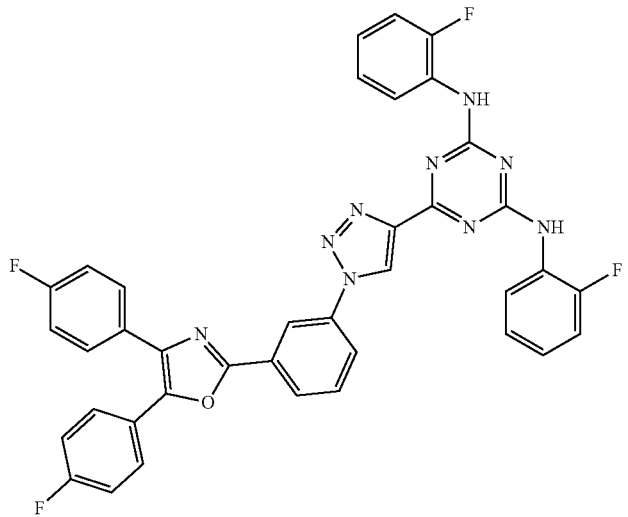

-continued
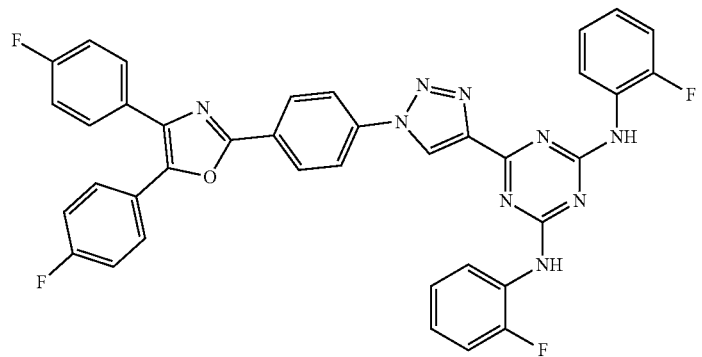
103
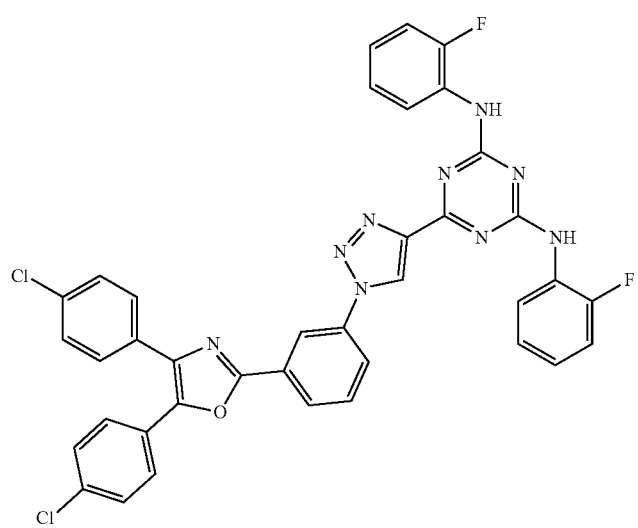
104
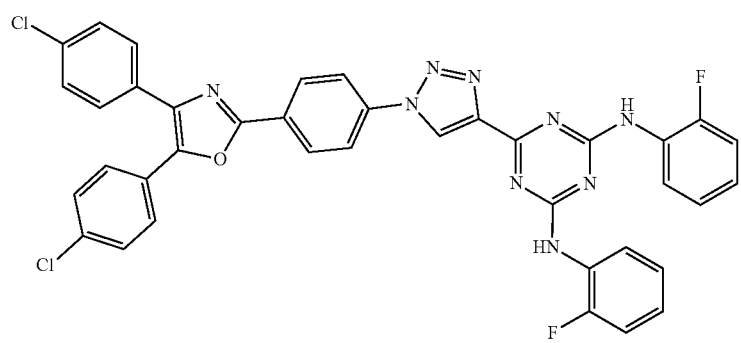
105

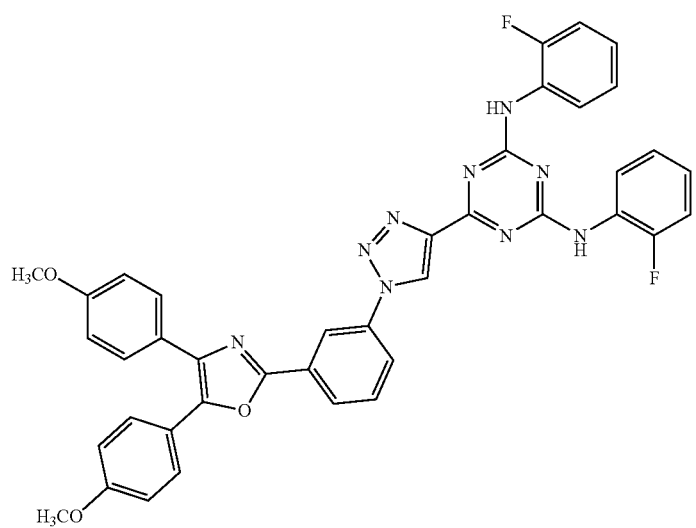
106
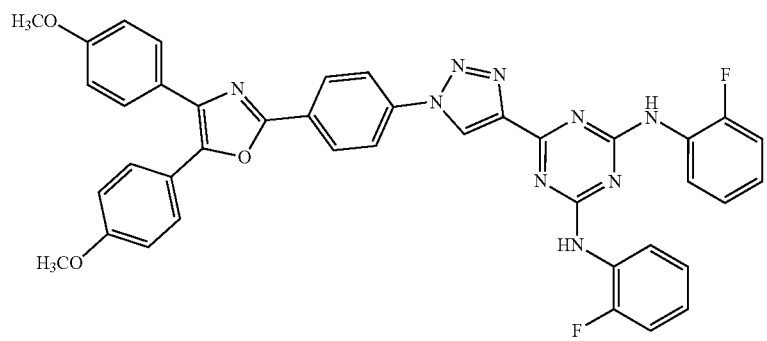
107
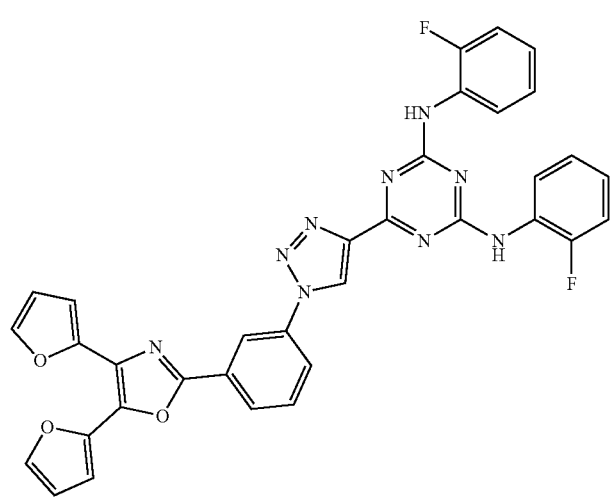
108

-continued
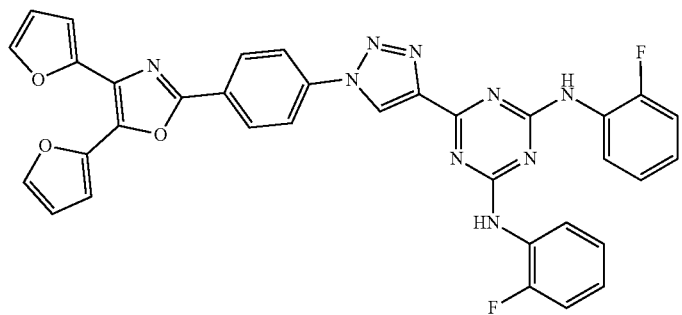
109
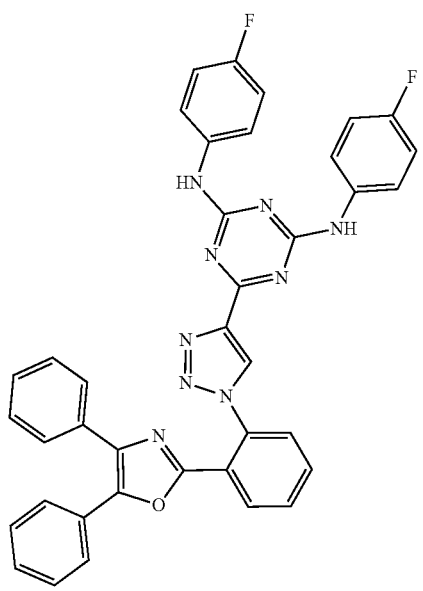
110
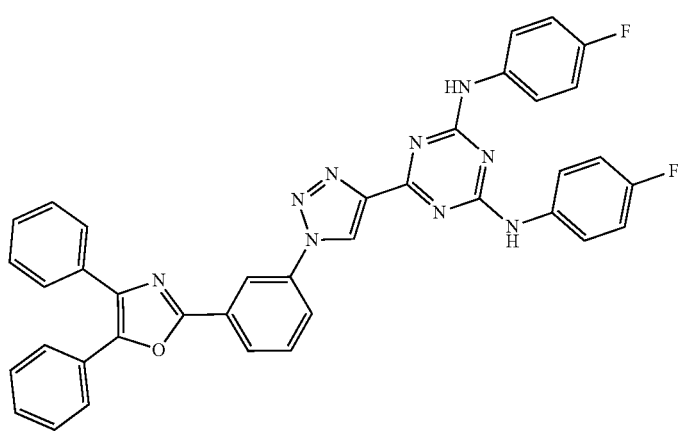
111

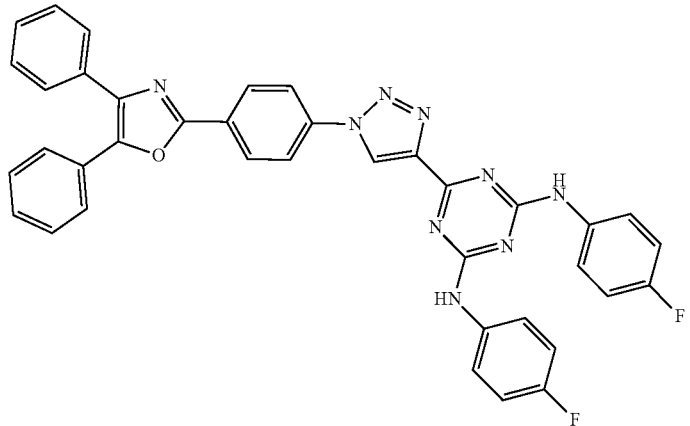
112
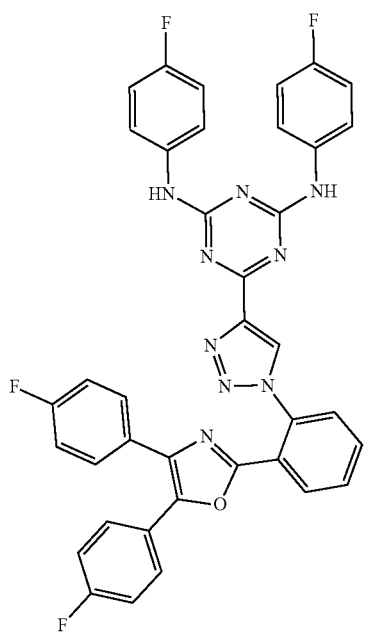
113
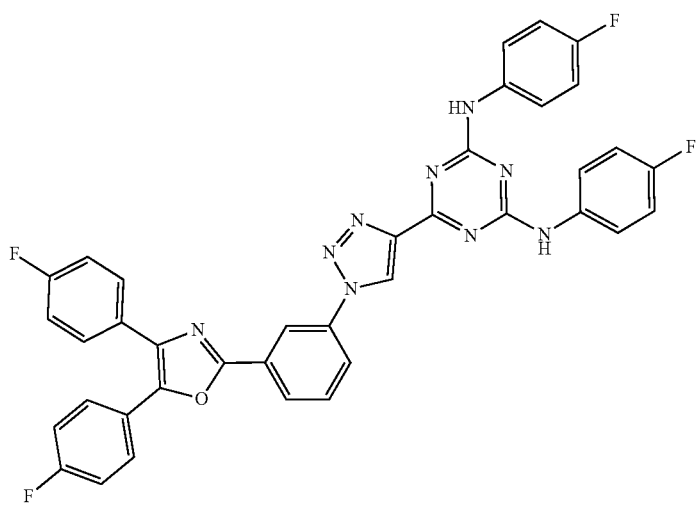
114

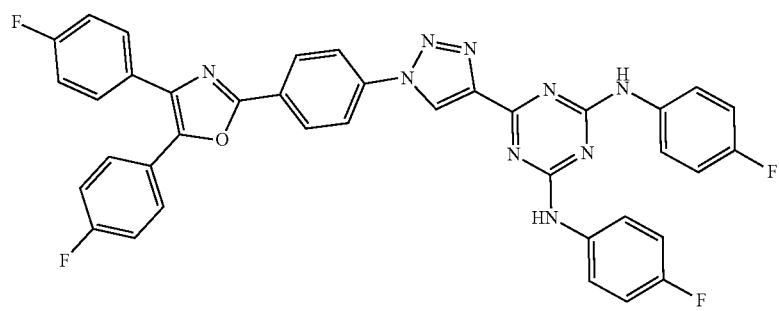
115
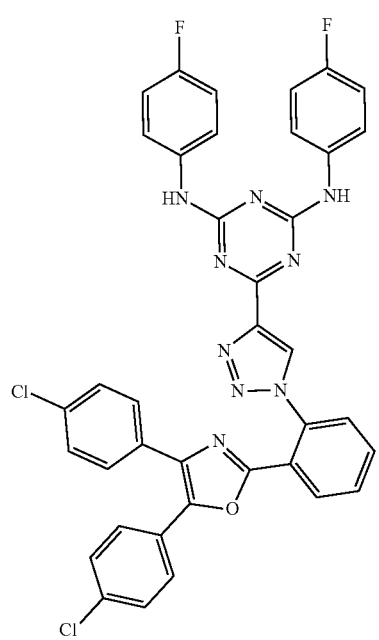
116

-continued
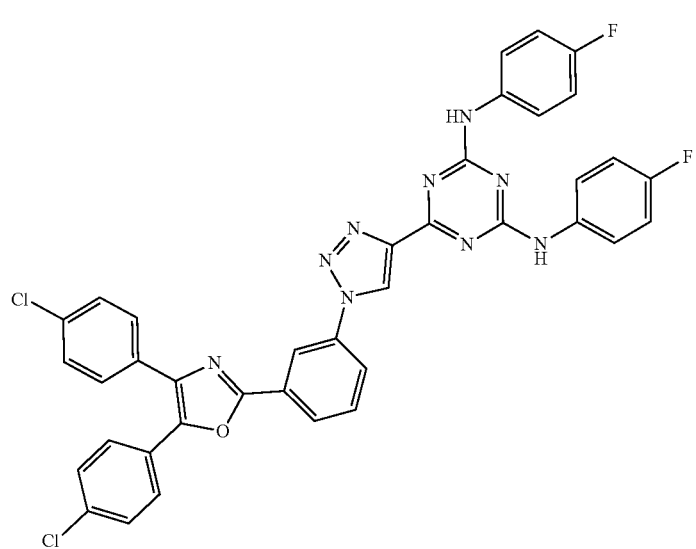
117
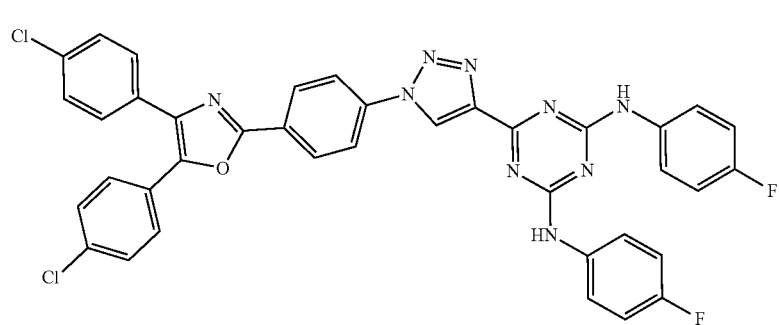
118

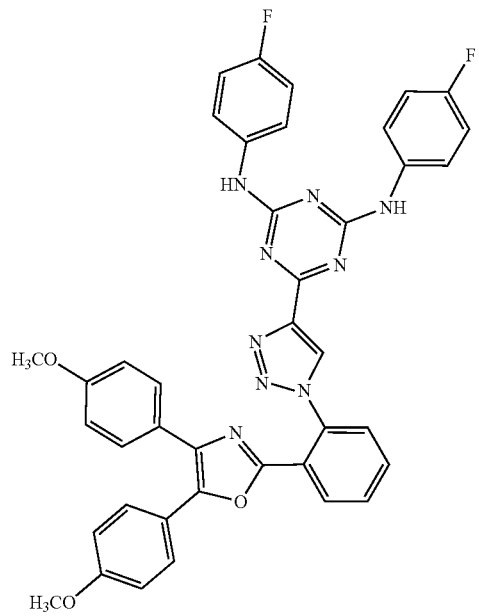
119
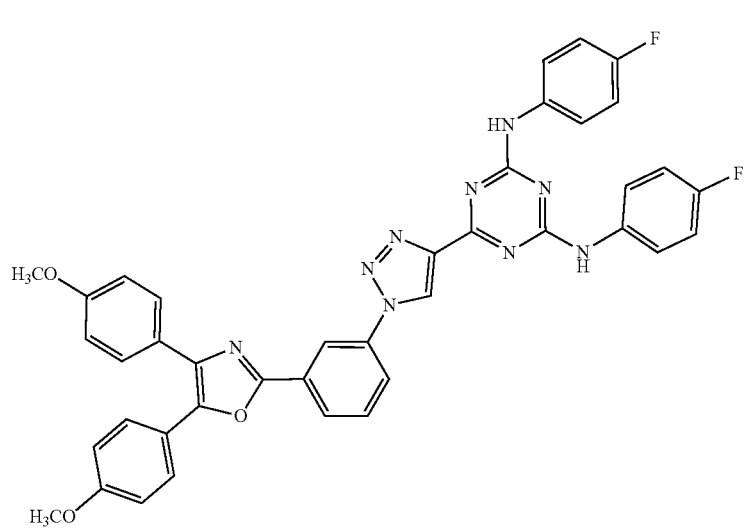
120

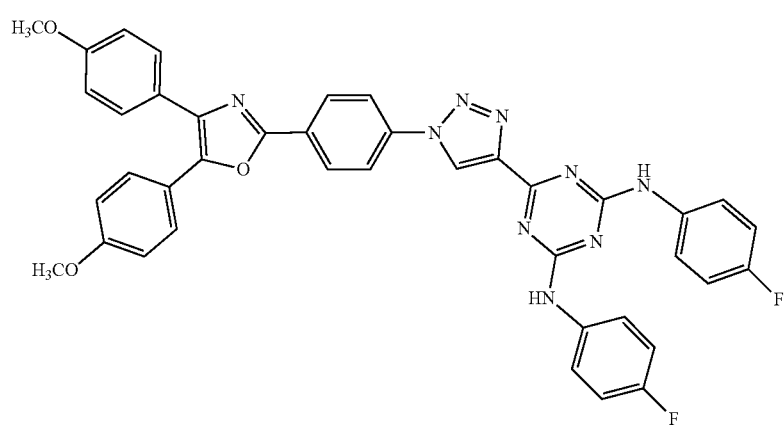

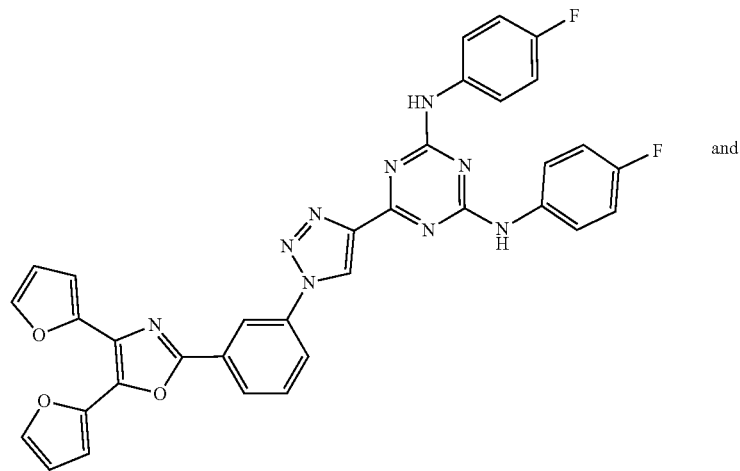
123
and
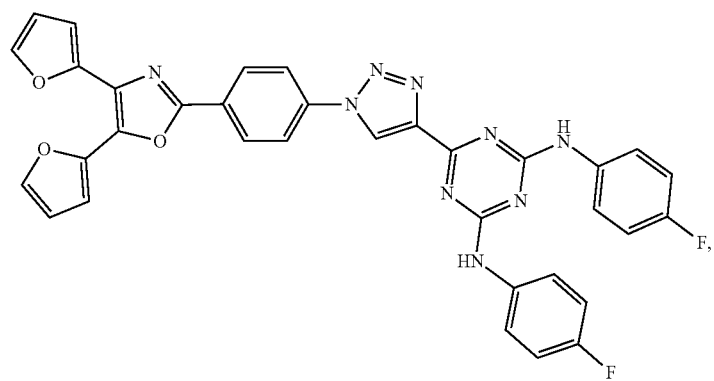
124
or a salt thereof.

12. A composition comprising a compound of formula I as described in claim 1 or a salt thereof and a physiologically acceptable carrier.

* * * * *